US007503891B2

(12) United States Patent
Green, II et al.

(10) Patent No.: US 7,503,891 B2
(45) Date of Patent: Mar. 17, 2009

(54) TISSUE STABILIZER AND METHODS OF USE

(75) Inventors: Harry Leonard Green, II, Santa Cruz, CA (US); Joshua K. Wallin, Sunnyvale, CA (US)

(73) Assignee: MAQUET Cardiovascular, LLC, San Jose, CA (US)

(*) Notice: Subject to any disclaimer, the term of this patent is extended or adjusted under 35 U.S.C. 154(b) by 0 days.

(21) Appl. No.: 10/272,036

(22) Filed: Oct. 15, 2002

(65) Prior Publication Data

US 2003/0088150 A1 May 8, 2003

Related U.S. Application Data

(63) Continuation of application No. 09/366,190, filed on Aug. 3, 1999, now Pat. No. 6,511,416.

(51) Int. Cl.
*A61F 2/00* (2006.01)

(52) U.S. Cl. .................... 600/37

(58) Field of Classification Search .................. 600/16, 600/36, 37, 201, 210, 213, 229, 209, 205, 600/208, 226–228, 231–235, 214, 206, 216; 128/897, 898; 606/1, 191, 205–208, 166
See application file for complete search history.

(56) References Cited

U.S. PATENT DOCUMENTS 452,131 A 5/1891 Haughawout
810,675 A 1/1906 Richter
1,706,500 A 3/1929 Smith
2,296,793 A 9/1942 Kirschbaum ................ 600/210
2,590,527 A 3/1952 Fluck
2,693,795 A 11/1954 Grieshaber .................. 128/20

(Continued)

FOREIGN PATENT DOCUMENTS

AU 713601 3/2000

(Continued)

OTHER PUBLICATIONS

U.S. Appl. No. 60/117,333 Looney et al., filed Jan. 24, 1999.

(Continued)

*Primary Examiner*—Samuel G Gilbert
(74) *Attorney, Agent, or Firm*—Law Office of Alan W. Cannon

(57) ABSTRACT

Devices and methods are disclosed for stabilizing tissue within a patient's body during a surgical operation to provide a relatively motionless surgical field. The devices involve tissue stabilizers which provide superior engagement with a tissue structure to be stabilized, for example the beating heart. The tissue stabilizer may have one or more stabilizer feet which provide for adjustment of the orientation of the features which engage the surface of the tissue structure. In one instance, the orientation may be adjusted to ensure the engaging features will be properly aligned with the surface of the tissue structure before engagement. In addition, once engaged with or connected to the tissue structure the orientation may be adjusted to yield an optimum surgical presentation of a portion of the tissue structure, for instance a coronary artery or the like. The tissue stabilizer may be configured to use friction, negative pressure, or both to engage the surface of the heart.

23 Claims, 20 Drawing Sheets

U.S. PATENT DOCUMENTS 2,863,444 A 12/1958 Winsten ...................... 128/20
3,392,722 A 7/1968 Jorgensen
3,584,822 A 6/1971 Oram
3,683,926 A 8/1972 Suzuki ................... 128/334 R
3,720,433 A 3/1973 Rosfelder .................... 294/64
3,783,873 A 1/1974 Jacobs ........................ 128/303
3,858,926 A 1/1975 Ottenhues .................... 294/64
3,882,855 A 5/1975 Schulte et al. ................ 128/20
3,983,863 A 10/1976 Janke et al. ................. 128/1 R
4,047,532 A 9/1977 Phillips et al. .............. 128/303
4,048,987 A 9/1977 Hurson ........................ 128/20
4,049,000 A 9/1977 Williams .................... 128/276
4,049,002 A 9/1977 Kletschka et al. ........... 128/318
4,052,980 A 10/1977 Grams et al. .................. 128/18
4,217,890 A 8/1980 Owens
4,226,228 A 10/1980 Shin et al. ..................... 128/20
4,230,119 A 10/1980 Blum ......................... 128/325
4,306,561 A 12/1981 de Medinaceli ............. 128/303
4,366,819 A 1/1983 Kaster ........................ 128/334
4,368,736 A 1/1983 Kaster ........................ 128/334
4,421,107 A 12/1983 Estes et al. .................... 128/20
4,428,368 A 1/1984 Torii .......................... 128/38
4,434,791 A 3/1984 Darnell ........................ 128/20
4,457,300 A 7/1984 Budde
4,461,284 A 7/1984 Fackler ........................ 128/20
4,492,229 A 1/1985 Grunwald ................... 128/303
4,617,916 A 10/1986 LeVahn et al.
4,627,421 A 12/1986 Symbas et al.
4,637,377 A 1/1987 Loop .......................... 128/1 R
4,646,747 A 3/1987 Lundback ................... 128/643
4,688,570 A 8/1987 Kramer et al. .............. 128/305
4,702,230 A 10/1987 Pelta .......................... 128/20
D293,470 S 12/1987 Adler
4,718,418 A 1/1988 L'Esperance, Jr. ....... 128/303.1
4,726,356 A 2/1988 Santilli et al.
4,726,358 A 2/1988 Brady ......................... 128/72
4,736,749 A 4/1988 Lundback ................... 128/643
4,747,395 A 5/1988 Brief .......................... 128/20
4,754,746 A 7/1988 Cox ........................... 128/20
4,803,984 A 2/1989 Narayanan et al. .......... 128/334
4,808,163 A 2/1989 Laub .......................... 604/105
4,827,926 A 5/1989 Carol
4,829,985 A 5/1989 Couetil
4,852,552 A 8/1989 Chaux
4,854,318 A 8/1989 Solem et al. ................ 128/346
4,858,552 A 8/1989 Glatt et al.
4,863,133 A 9/1989 Bonnell ...................... 248/278
4,865,019 A 9/1989 Phillips ....................... 128/20
4,884,559 A 12/1989 Collins ........................ 128/17
4,925,443 A 5/1990 Heilman et al. ............... 600/16
4,949,707 A 8/1990 LeVahn et al. ................ 128/20
4,949,927 A 8/1990 Madocks et al.
4,955,896 A 9/1990 Freeman ..................... 606/210
4,957,477 A 9/1990 Lundbach
4,962,758 A 10/1990 Lasner et al. ................. 128/41
4,971,037 A 11/1990 Pelta
4,973,300 A 11/1990 Wright ........................ 600/37
4,989,587 A 2/1991 Farley ......................... 128/20
4,991,578 A 2/1991 Cohen ........................ 128/419
4,993,862 A 2/1991 Pelta
5,009,660 A 4/1991 Clapham .................... 606/166
5,011,469 A 4/1991 Buckberg et al. .............. 604/4
5,019,086 A 5/1991 Neward
5,025,779 A 6/1991 Bugge
5,036,868 A 8/1991 Berggren et al. ............ 128/898
5,037,428 A 8/1991 Picha et al. ................. 606/155
5,052,373 A 10/1991 Michelson ................... 128/20
5,053,041 A 10/1991 Ansari et al. ................ 606/148
5,080,088 A 1/1992 LeVahn ....................... 128/20
5,098,369 A 3/1992 Heilman et al. ............... 600/16
5,119,804 A 6/1992 Anstadt ...................... 128/64
5,125,395 A 6/1992 Adair
5,131,905 A 7/1992 Grooters ...................... 600/16
5,133,724 A 7/1992 Wilson, Jr. et al. .......... 606/151
5,139,517 A 8/1992 Corral
5,150,706 A 9/1992 Cox et al.
5,152,777 A 10/1992 Goldberg et al.
5,159,921 A 11/1992 Hoover ........................ 128/20
RE34,150 E 12/1992 Santilli et al.
5,167,223 A 12/1992 Koros et al. .................. 128/20
5,171,254 A 12/1992 Sher .......................... 606/166
5,196,003 A 3/1993 Bilweis
5,231,974 A 8/1993 Giglio et al.
5,256,132 A 10/1993 Snyders
5,287,861 A 2/1994 Wilk .......................... 128/898
5,293,863 A 3/1994 Zhu et al. ..................... 128/20
5,300,087 A 4/1994 Knoepfler ................... 606/207
5,336,252 A 8/1994 Cohen ........................ 607/119
5,348,259 A 9/1994 Blanco et al.
5,363,882 A 11/1994 Chikama
5,382,756 A 1/1995 Dagan ......................... 174/92
5,383,840 A 1/1995 Heilman et al. ............... 600/17
5,417,709 A 5/1995 Slater ......................... 606/205
5,425,705 A 6/1995 Evard et al.
5,437,651 A 8/1995 Todd et al. .................. 604/313
5,452,733 A 9/1995 Sterman et al. ............. 128/898
5,453,078 A 9/1995 Valentine et al.
5,467,763 A 11/1995 McMahon et al. .......... 600/201
5,480,425 A 1/1996 Ogilive
5,498,256 A 3/1996 Furnish ........................ 606/1
5,503,617 A 4/1996 Jako
5,509,890 A 4/1996 Kazama ....................... 600/37
5,512,037 A 4/1996 Russell et al. ............... 600/206
5,514,075 A 5/1996 Moll et al. .................. 600/202
5,514,076 A 5/1996 Ley ........................... 600/206
5,520,610 A 5/1996 Giglio et al. ................ 600/233
5,522,819 A 6/1996 Graves et al.
5,529,571 A 6/1996 Daniel ........................ 600/219
5,536,251 A 7/1996 Evard et al.
5,547,458 A 8/1996 Ortiz et al. .................. 600/204
5,569,274 A 10/1996 Rapacki et al.
5,571,074 A 11/1996 Buckman, Jr. et al.
5,571,215 A 11/1996 Sterman et al.
5,573,496 A 11/1996 McPherson et al. ......... 600/217
5,582,580 A 12/1996 Buckman, Jr. et al.
5,607,421 A 3/1997 Jeevanandam et al. ........ 606/15
5,607,446 A 3/1997 Beehler et al. .............. 606/198
5,613,937 A 3/1997 Garrison et al. ............. 600/201
5,632,746 A 5/1997 Middleman et al.
5,651,378 A 7/1997 Matheny et al. ............. 128/898
5,662,300 A 9/1997 Michelson
5,667,480 A 9/1997 Knight et al.
5,713,951 A 2/1998 Garrison et al.
5,727,569 A 3/1998 Benetti et al. ............... 128/898
5,728,151 A 3/1998 Garrison et al.
5,730,757 A 3/1998 Benetti et al. ............... 606/198
5,735,290 A 4/1998 Sterman et al.
5,749,892 A 5/1998 Vierra et al. ................ 600/204
5,755,660 A 5/1998 Tyagi
5,766,151 A 6/1998 Valley et al.
5,772,583 A 6/1998 Wright et al.
5,782,746 A 7/1998 Wright ........................ 600/37
5,795,291 A 8/1998 Koros et al. ................. 600/232
5,797,960 A 8/1998 Stevens et al.
5,799,661 A * 9/1998 Boyd et al. ................. 128/898
5,807,243 A 9/1998 Vierra et al. ................ 600/204
5,813,410 A 9/1998 Levin ......................... 128/897
5,836,311 A 11/1998 Borst et al. ................. 128/897
5,846,187 A 12/1998 Wells et al. ................. 600/201
5,846,193 A 12/1998 Wright ...................... 600/215
5,846,194 A 12/1998 Wasson et al.
5,865,730 A 2/1999 Fox et al. .................... 600/228
5,868,770 A 2/1999 Rygaard
5,875,782 A 3/1999 Ferrari et al. ............... 128/898

| | | | | |
|---|---|---|---|---|
| 5,876,332 | A | 3/1999 | Looney | |
| 5,879,291 | A | 3/1999 | Kolata et al. | 600/227 |
| 5,882,299 | A | 3/1999 | Rastegar et al. | |
| 5,885,271 | A | 3/1999 | Hamilton et al. | 606/1 |
| 5,888,247 | A | 3/1999 | Benetti | 623/66 |
| 5,891,017 | A | 4/1999 | Sindle et al. | |
| 5,894,843 | A | 4/1999 | Benetti et al. | 128/898 |
| 5,906,607 | A | 5/1999 | Taylor et al. | 606/1 |
| 5,908,382 | A | 6/1999 | Koros et al. | 600/232 |
| 5,913,876 | A | 6/1999 | Taylor et al. | 607/2 |
| 5,927,284 | A | 7/1999 | Borst et al. | 128/898 |
| 5,944,658 | A | 8/1999 | Koros et al. | |
| 5,944,736 | A | 8/1999 | Taylor et al. | 606/198 |
| 5,947,125 | A | 9/1999 | Benetti | 128/898 |
| 5,947,896 | A | 9/1999 | Sherts et al. | |
| 5,957,835 | A | 9/1999 | Anderson et al. | |
| 5,961,481 | A | 10/1999 | Sterman et al. | |
| 5,967,972 | A | 10/1999 | Santilli et al. | 600/232 |
| 5,967,973 | A | 10/1999 | Sherts et al. | |
| 5,976,080 | A | 11/1999 | Farascioni | |
| 5,976,171 | A | 11/1999 | Taylor | 606/198 |
| 5,984,864 | A * | 11/1999 | Fox et al. | 600/201 |
| 5,984,865 | A | 11/1999 | Farley et al. | 600/213 |
| 5,984,867 | A | 11/1999 | Deckman et al. | 600/232 |
| 6,007,486 | A | 12/1999 | Hunt et al. | |
| 6,007,523 | A | 12/1999 | Mangosong | |
| 6,010,531 | A | 1/2000 | Donlon et al. | |
| 6,013,027 | A | 1/2000 | Khan et al. | |
| 6,015,378 | A | 1/2000 | Borst et al. | |
| 6,017,304 | A | 1/2000 | Vierra et al. | 600/204 |
| 6,019,722 | A | 2/2000 | Spence et al. | |
| 6,027,476 | A | 2/2000 | Sterman et al. | |
| 6,029,671 | A | 2/2000 | Stevens et al. | |
| 6,030,340 | A | 2/2000 | Maffei et al. | |
| D421,803 | S | 3/2000 | Koros et al. | |
| 6,032,672 | A | 3/2000 | Taylor | |
| 6,033,362 | A | 3/2000 | Cohn | |
| 6,050,266 | A | 4/2000 | Benetti et al. | 128/898 |
| 6,063,021 | A | 5/2000 | Hossain et al. | |
| 6,071,295 | A | 6/2000 | Takahashi | 606/191 |
| 6,099,468 | A | 8/2000 | Santilli et al. | 600/232 |
| 6,102,853 | A | 8/2000 | Scirica et al. | |
| 6,102,854 | A | 8/2000 | Carfier et al. | 600/228 |
| 6,113,534 | A * | 9/2000 | Koros et al. | 600/213 |
| 6,139,492 | A | 10/2000 | Vierra et al. | 600/204 |
| 6,149,583 | A | 11/2000 | Vierra et al. | |
| 6,152,874 | A | 11/2000 | Looney et al. | |
| 6,159,201 | A * | 12/2000 | Hamilton et al. | 606/1 |
| 6,167,889 | B1 | 1/2001 | Benetti | |
| 6,183,486 | B1 | 2/2001 | Snow et al. | |
| 6,190,311 | B1 | 2/2001 | Glines et al. | |
| 6,193,652 | B1 | 2/2001 | Berky et al. | |
| 6,193,732 | B1 | 2/2001 | Frantzen et al. | |
| 6,200,263 | B1 | 3/2001 | Person | |
| 6,213,940 | B1 | 4/2001 | Sherts et al. | |
| 6,213,941 | B1 | 4/2001 | Benetti et al. | |
| 6,231,506 | B1 | 5/2001 | Hu et al. | |
| 6,258,023 | B1 * | 7/2001 | Rogers et al. | 600/37 |
| 6,264,605 | B1 | 7/2001 | Scirica et al. | 600/227 |
| 6,283,912 | B1 | 9/2001 | Hu et al. | 600/232 |
| 6,290,644 | B1 | 9/2001 | Green, II et al. | 600/235 |
| 6,315,717 | B1 | 11/2001 | Benetti et al. | 600/210 |
| 6,331,158 | B1 | 12/2001 | Hu et al. | 600/232 |
| 6,334,843 | B1 | 1/2002 | Borst et al. | 600/37 |
| 6,336,898 | B1 | 1/2002 | Borst et al. | 600/37 |
| 6,346,077 | B1 | 2/2002 | Taylor et al. | 600/204 |
| 6,348,036 | B1 | 2/2002 | Looney et al. | |
| 6,364,826 | B1 | 4/2002 | Borst et al. | 600/37 |
| 6,371,906 | B1 | 4/2002 | Borst et al. | 600/37 |
| 6,394,948 | B1 | 5/2002 | Borst et al. | 600/37 |
| 6,394,951 | B1 | 5/2002 | Taylor et al. | 600/210 |
| 6,406,424 | B1 | 6/2002 | Williamson, IV et al. | 600/201 |
| 6,475,142 | B1 | 11/2002 | Parsons et al. | |
| 6,626,830 | B1 * | 9/2003 | Califiore et al. | 600/229 |
| 6,701,930 | B2 | 3/2004 | Benetti et al. | |

FOREIGN PATENT DOCUMENTS

| | | |
|---|---|---|
| CA | 2197608 | 2/2000 |
| DE | 31 38 589 A1 | 4/1983 |
| DE | 0 293 760 A2 | 12/1988 |
| DE | 0 293 760 A3 | 12/1988 |
| DE | 0 293 760 B1 | 12/1988 |
| DE | 90 04513 | 6/1990 |
| DE | 41 39 695 A1 | 6/1993 |
| EP | 0 630 629 A1 | 5/1994 |
| EP | 0 668 058 A1 | 2/1995 |
| EP | 0791 330 A2 | 8/1997 |
| EP | 0 803 228 A1 | 10/1997 |
| EP | 0 808 606 A1 | 11/1997 |
| EP | 0 919 193 A1 | 6/1999 |
| EP | 0 993 806 A2 | 4/2000 |
| FR | 473451 | 1/1915 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A2 | 9/1997 |
| WO | WO 97/32514 A3 | 9/1997 |
| WO | WO 97/40752 | 11/1997 |
| WO | WO 98/27869 | 7/1998 |
| WO | WO 98/48703 | 11/1998 |
| WO | WO 98/49944 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 99/60930 A2 | 12/1999 |
| WO | WO 99/60930 A3 | 12/1999 |
| WO | WO 00/06041 | 2/2000 |
| WO | WO 00/10466 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

U.S. Appl. No. 09/345,859 Looney et al., filed Jul. 1, 1999.

U.S. Appl. No. 09/438,670 Parsons, et al., filed Nov. 12, 1999.

U.S. Appl. No. 09/489,274 Brown et al., filed Jan. 21, 2000.

C.W. Akins et al., "*Preservation of Interventricular Septal Function in Patients Having Coronary Artery Bypass Grafts Without Cardiopulmonary Bypass*," American Heart Journal, vol. 107, No. 2 Feb. 1984, pp. 304-309.

Ancalmo, N. and J. L. Ochsner: "*A Modified Sternal Retractor*," Ann. Thorac, Surg. 21 (1976) 174.

Angelini, G.D., M.D. et al., "*A Fiber-Optic Retractor for Harvesting the Internal Mammary Artery*," Ann. Thorac. Surg. (1990; 50:314-5).

Angelini, G.D., M.D., "*A Simple, Inexpensive Method of Heart Retraction During Coronary Artery Bypass Surgery*," Ann. Thora. Surg 46:46-247, Aug. 1988.

Anstadt, M.P. MD et al., "*Direct Mechanical Ventricular Actuation for Cardiac Arrest in Humans*," Chest, vol. 100, No. 1, Jul. 1991, pp. 86-92.

Antinori, C. et al., "*A Method of Retraction During Reoperative Coronary Operations Using the Favaloro Retractor*," The Society of Thoracic Surgeons: 1989.

Archer, R. DO et al., "*Coronary Artery Revascularization Without Cardiiopulmonary Bypass*," Texas Heart Institute Journal, vol. 11, No. 1, Mar. 1984, pp. 52-57.

Arom, K.V., et al., "Mini-Sternotomy for Coronary Artery Bypass Grafting," The Annals of Thoracic Surgery 1996; 61:1271-2.

Arom, K.V., et al., "Mini-Sternotomy for Coronary Artery Bypass Grafting," The Annals of Thoracic Surgery 1996; 62:1884-85.

Ballantyne, C.M. et al. "*Delayed Recovery of Severely 'Stunned' Myocardium With the Support of a Left Ventricular Assist Device after Coronary Artery Bypass Graft Surgery*," Journal of the American College of Cardiology, vol. 10, No. 3, Sep. 1987, pp. 710-712.

Bedellino, M.M., et al., "*The Cardiac Rag—Simple Exposure of the Heart*," Texas Heart Institute Journal, vol. 15, No. 2, 1988, 134-35.

Beg, R.A. et al., "*Internal Mammary Retractor*," Ann Thorac, Surg., vol. 39, No. 1, Jan. 1985, pp. 286-287.

Benetti, F. J. et al., "*Direct Coronary Surgery with Saphenous Vein Bypass Without Either Cardiopulmonary Bypass Graft or Cardiac Arrest*," The Journal of Cardiovascular Surgery, vol. 26, No. 3, May-Jun. 1985, pp. 217-222.

Benetti, F. J. et al., "*Direct Myocardial Revascularization Without Extracorporeal Circulation*," Chest, vol. 100, No. 2, Aug. 1991, pp. 312-316.

Benetti, F. J., "*Coronary Revascularization with Arterial Conduits via a Small Thoracotomy and Assisted by Thoracoscopy, Although Without Cardiopulmonary Bypass*," Cor Europaeum 4 (1) 22-24 (1995).

Bonatti, et al., "Single Coronary Artery Bypass Grafting—a Comparison Between Minimally Invasive 'Off Pump' Techniques and Conventional Procedures," European Journal of Cardio-Thoracic Surgery 14, (supp. 1) S7-S12 1998.

Borst, C. et al., "*Coronary Artery Grafting Without Cardiopulmonary Bypass and Without Interruption of Native Coronary Flow Using A Novel Anastomosis Site Restraining Device*," ("Octopus") JACC, vol. 27 No. 6, May 1996:1356-6.

Borst C., et al. "*Regional Cardiac Wall Immobilization for Open Chest and Closes Chest Coronary Artery Bypass Grafting on the Beating Heart: The Octopus Method*," Abstract from the 68$^{th}$ Scientific Sessions.

British Heart Journal, "Coronary Surgery Without Cardiopulmonary Bypass," pp. 203-205, 1995.

Bugge, M., "*A New Internal Mammary Artery Retractor*," Thorac. Cardiovasc Surgeon 38, pp. 316-317 (1990).

Buffolo, E., et al., "*Direct Myocardial Revascularization Without Cardiopulmonary Bypass*," Thorac. Cardiovasc. Surgeon, 33 (1985) pp. 26-29.

Calafiore, A. M., et al., "*Minimally Invasive Coronary Artery Bypass Grafting*," The Annals of Thoracic Surgery, 62:1545-8, 1996.

Campalani, G., M.D., et al., "*A New Self-Retaining Internal Mammary Artery Retractor*," J. Cardiovas. Surg. 28, 1987, pp. 347-348.

Cartier, R, MD., "*Triple Coronary Artery Revascularization on the Stabilized Beating Heart: Initial Experience*," Montreal Heart Institute, CJS, vol. 41, No. 4, pp. 283-288, Aug. 1998.

Chaux, A. and C. Blanche, "*A New Concept in Sternal Retraction: Applications for Internal Mammary Artery Dissection and Valve Replacement Surgery*," Ann. Thorac. Surg. 42, Oct. 1986, pp. 473-474.

Cooley, D. A., "*Limited Access Myocardial Revascularization*," Texas Heart Institute Journal, pp. 81-84, vol. 23, No. 2, 1996.

*Correspondence and Brief Communications*, Archives of Surgery—vol. 115, 1136-37, Sep. 1980.

Cremer, J, MD, "*Off-Bypass Coronary Bypass Grafting Via Minithoracotomy Using Mechanical Epicardial Stabilization*," The Annals of Thoracic Surgery, 63:S79-83, 1997.

Delacroix-Chevalier Surgical Instruments, IMA Saving Packages Brochure.

DelRossi, A J and Lemole, GM, "*A New Retractor to Aid in Coronary Artery Surgery*," The Annals of Thoracic Surgery, vol. 36, No. 1, 101-102, Jul. 1983.

Fanning, W. J. et al., "*Reoperative Coronary Artery Bypass Grafting Without Cardiopulmonary Bypass*," The Annals of Thoracic Surgery, vol. 55, No. 2, Feb. 1993, pp. 486-489.

Favaloro, R. G., et al. "*Direct Myocardial Revascularization by Saphenous Vein Graft*," The Annals of Thoracic Surgery, vol. 10, No. 2, Aug. 1970, pp. 97-111.

Fonger, J. D., et al., "*Enhanced Preservation of Acutely Ischmenic Myocardium with Transeptal Left Ventricular Assist*," The Annals of Thoracic Surgery, vol. 57, No. 3, Mar. 1994, pp. 570-575.

Gacioch, G. M., MD, et al., "*Cardiogenic Shock Complicating Acute Myocardial Infarction: The Use of Coronary Angioplasty and the Integration of the New Support Device into Patient Management*," Journal of the American College of Cardiology, vol. 19, No. 3, Mar. 1, 1992.

Green, GE., "*Technique of Internal Mammary-Coronary Artery Anastomosis*," The Journal of Cardiovascular Surgery, 78:455-79, 1979.

Groopman, J., "*Heart Surgery, Unplugged; Making the Coronary Bypass Safer, Cheaper, and Easier*," The New Yorker, Jan. 11, 1999, pp. 43-46, 50-51.

Guzman, F. M.D., "*Transient Radial Nerve Injury Related to the Use of A Self Retraining Retractor for Internal Mammary Artery Dissection*," J. Cardiovasc. Surg. 30, 1989, pp. 1015-1016.

Hasan, R. I., et al., "*Technique of Dissecting the Internal Mammary After Using The Moussalli Bar*," European Journal of Cardio Thoracic Surgery, 4:571-572, 1990.

Itoh, Toshiaki, M.D., et al., "*New Modification of a Mammary Artery Retractor*," Ann. Thorac. Surg. 9, 1994; 57:1670-1.

Izzat, M. B. et al., "*Cardiac Stabilizer for Minimally Invasive Direct Coronary Artery Bypass*," Ann Thorac Surg, 1997; 64:570-1.

Japanese Journal of Thoracic Surgery, vol. 42, No. 2, 1989.

Japanese Article "*Heart Retractor*".

Kolessov, V.I., M.D., "*Mammary Artery-Coronary Artery Anastomosis as Method of Treatment for Angina Pectoris*," Thoracic and Cardiovascular Surgery, vol. 54, No. 4, Oct. 1967, pp. 535-544.

Kazama, S. et al., "*Fabric Heart Retractor for Coronary Artery Bypass Operations*," The Annals of Thoracic Surgery, 55:1582-3, 1993.

Konishi, T. MD, et al., "Hybrid-Type Stabilizer for Off-Pump Direct Coronary Artery Bypass Grafting," Annals of Thoracic Surgery 66:961-2, 1998.

Kresh, J. Y., et al., "*Heart-Mechanical Assist Device Interaction*," Trans. Am. Soc. Artif. Intern. Organs, vol. XXXII, 1986, pp. 437-443.

Lavergne, et al., "*Transcatheter Radiofrequency Ablation of Atrial Tissue Using a Suction Catheter*," PACE, vol. 12, Jan. 1989, Part II, pp. 177-186.

Lonn, U., M.D., et al., "*Coronary Artery Operation Supported by the Hemopump: An Experimental Study on Pigs*," The Annals of Thoracic Surgery, vol. 58, No. 1, Jul. 1994, pp. 516-523.

Matsuura, A., et al., "*A New Device for Exposing the Circumflex Coronary Artery*," The Annals of Thoracic Surgery, 59:1249-50, 1995, pp. 1249-1250.

McGee, M. G.,et al., "*Extended Clinical Support with an Implantable Left Ventricular Assist Device*," Trans. Am. Soc. Artif. Intern. Organs, vol. XXXV, 1989, pp. 614-616.

McKeown, P.P. et al., "*A Modified Sternal Retractor for Exposure of the Internal Mammary Artery*," Ann. Thorac. Surg. 32 (1981) 619.

Ochsner, J. L., et al., "*Surgical Management of Diseased Intracavitary Coronary Arteries*," The Annals of Thoracic Surgery, vol. 38, No. 4, July, pp. 356-362, Oct. 1984.

Parsonnet, V. MD, et al., "*Graduated probes for Coronary Bypass Surgery*," The Journal of Thoracic and Cardiovascular Surgery, vol. 68, No. 3, 424-26 (Sep. 1974).

Parsonnet, V. MD, et al., "*Self—Retaining Epicardial Retractor for Aortocoronary Bypass Surgery*," The Journal of Thoracic and Cardiovascular Surgery, 629-30 1979.

Perrault, L. et al., "Snaring of the Target Vessel in Less Invasive Bypass Operations Does Not Cause Endothelial Dysfunction," The Society of Thoracic Surgeons, pp. 751-755, 1997.

Pfister, A. J. M.D., et al., "*Coronary Artery Bypass Without Cardiopulmonary Bypass*," The Annals of Thoracic Surgery, vol. 54, No. 6, Dec. 1992, pp. 1085-1092.

Phillips, Steven J., M.D. et al., "*A Versatile Retractor for Use in Harvesting the Internal Mammary Artery and Performing Standard Cardiac Operations*," J. Thorac. Cardiovasc. Surg. (1989; 97:633-5).
Pilling Surgical Instruments, A Rusch International Company Brochure.
Pittman, John, M.D., et al., "*Improved Visualization of the Internal Mammary Artery with a New Retractor System*," Ann. Thorac. Surg., 1989; 48:869-70.
Riahi, M.,et al., "*A Simple Technique and Device to Provide a Bloodless Operative Field in Coronary Artery Surgery Without Cross-Clamping the Aorta*," The Journal of Thoracic and Cardiovascular Surgery, vol. 66, No. 6, Dec. 1973, pp. 974-978.
Richenbacher, W. E., MD, et al., "*Current Status of Cardiac Surgery: A 40-Year Review*," Journal of American College of Cardiology, vol. 14, No. 3, pp. 535-544.
Robicsek, F., "*Aortic Spoon-Jaw Clamp for Aorto-Saphenous Vein Anastomosis*," J. Card. Surg., 1995; 10:583-585.
Robinson, M. C., et al., "*A Minimally Invasive Surgical Method for Coronary Revascularization—Preliminary Experience in Five Patients*," Circulation, Oct. 15, 1995, vol. 92, No. 8, 1-176.
Rousou, J. et al., "*Cardiac Retractor for Coronary Bypass Operations*," Ann Thorac. Surg, 1991; 52:877-8.
Roux, D., M.D. et al., "*Internal Mammary Artery Dissection: A Three Dimensional Sternal Retractor*," J. Cardiovasc. Surg., 1989; 30:996-7.
Roux, D., M.D. et al., "*New Helper Instrument in Cardiac Surgery*," The Society of Thoracic Surgeons, 1989.
Ruzevich, S. A., et al., "*Long-Term Follow-Up of Survivors of Postcardiotomy Circulatory Support*," Trans. Am. Soc. Artif. Intern. Organs, vol. XXXIV, 1988, pp. 116-124.
Scholz, K. H., et al., "*Transfemoral Placement of the Left Ventricular Assist Device 'Hemopump' During Mechanical Resuscitation*," Thoracic and Cardiovascular Surgeon, vol. 38 (1990) pp. 69-72.
Stevens, et al., "*Closed Chest Coronary Artery Bypass With Cardioplegic Arrest in the Dog*," 67$^{th}$ Scientific Session, 238, I-251, 1999.
Trapp, W. G. and Bisarya, R., "*To Use or Not To Use the Pump Oxygenator in Coronary Bypass Operations*," The Annals of Thoracic Surgery, vol. 19, No. 1, Jan. 1975, pp. 108-109.
Trapp, et al., "*Placement of Coronary Artery Bypass Graft without Pump Oxygenator*," Journal of the Society of Thoracic Surgeons and The Southern Thoracic Surgeons Assn. vol. 19 , No. 1, Jan. 1975.
USSC Cardiovascular Thora-Lift™, United States Surgical Corporation, Norwalk, Connecticut, Product Brochure, 1999.
Vincent, J.G., "*A Compact Single Post Internal Mammary Artery Dissection Retractor*," Eur. J. Cardio-Thor. Surg. 3 (1989) 276-277.
Westaby, S. et al., "Less Invasive Coronary Surgery: Consensus From the Oxford Meeting," The Annals of Thoracic Surgery, 62:924-31, 1996.
Zumbro, G. L. et al., "*A Prospective Evaluation of the Pulsatile Assist Device*," The Annals of Thoracic Surgery, vol. 28, No. 2, Aug. 1979, pp. 269-273.
Calvin (1990) "Circumflex Exposure Using a Cardiac Sling." Ann Thorac Surg., vol. 49:833-4.
Eguchi (1987) "A Special Retracter for Stabilizing the Heart During Circumflex Coronary Grafting." *Kyobu Geka*, vol. 40(1):39-40.
Janke "Heart Support for Coronary Bypass Surgery Involving the Circumflex Artery System." *The Journal of Thoracic and Cardiovascular Surgery*, vol. 67(6):883-4, 1999.
Konishi, T. MD, et al., "*Hybrid-Type Stabilizer for Off-Pump Direct Coronary Artery Bypass Grafting*," Annals of Thoracic Surgery 66:961-2, 1998.
Splittgerber et al. (1996) "Exposing the Circumflex Coronary Artery: The Heartflip Technique." *Ann Thorac Surg.*, vol. 61:1019-20.

* cited by examiner 200
122
125
124
210
215
215
215
141
135
205
142
125
144
215

200
117
115
119
124
130
135
155
152
218
222
154
128
223
122
202
214
208
212
205
140
210
141

300
117
115
119
124
307
306
130
135
155
152
222
128
154
223
122
202
303
302
304
301
308
305
140
310
141

458
459
457
449
437
435
450
456
455
455'

467
449
437
435
460
466
465

550
560
560
560
560
555
557
17
561
554
561
553
561
552
561
551
556
17

560
560
560
563
560
555
557
561
561
561
561
562
550
554
553
552
551

725
740
737
735
736
732
742
738
734
730

TISSUE STABILIZER AND METHODS OF USE

CROSS REFERENCE TO RELATED APPLICATIONS

This application is a continuation of U.S. patent application Ser. No. 09/366,190, filed Aug. 3, 1999, now is a U.S. Pat. No. 6,511,416 which is herein incorporated by reference in its entirety.

FIELD OF THE INVENTION

The present invention relates generally to surgical instruments, and more particularly to methods and apparatus for stabilizing or immobilizing tissue during surgery. The tissue stabilizers described herein are particularly useful for stabilizing the beating heart during coronary artery bypass graft surgery.

BACKGROUND OF THE INVENTION

Certain surgical procedures require the surgeon to perform delicate operations on tissues within the body that are moving or otherwise unstable. The ability to stabilize or immobilize the surgical site provides greatly improved surgical accuracy and precision and reduces the time required to complete a particular procedure. A large and growing number of surgeons, for example, are routinely performing successful coronary artery bypass graft (CABG) surgery on the beating heart by temporarily stabilizing or immobilizing a localized area of the beating heart. Methods and apparatus for performing a CABG procedure on the beating heart are described in U.S. Pat. Nos. 5,894,843 and 5,727,569 to Benetti et al., the entirety of which is herein incorporated by reference.

In a typical CABG procedure, a blocked or restricted section of coronary artery, which normally supplies blood to some portion of the heart, is bypassed using a source vessel or a graft vessel to re-establish blood flow to the artery downstream of the blockage. This procedure requires the surgeon to create a fluid connection, or anastomosis, between the source or graft vessel and an arteriotomy or incision in the coronary artery. Forming an anastomosis between two vessels in this manner is a particularly delicate procedure requiring the precise placement of tiny sutures in the tissue surrounding the arteriotomy in the coronary artery and the source or graft vessel.

The rigors of creating a surgical anastomosis between a coronary artery and a graft or source vessel demands that the target site for the anastomosis be substantially motionless. To this end, a number of devices have been developed which are directed to stabilizing a target site on the beating heart for the purpose of completing a cardiac surgical procedure, such as completing an anastomosis. Representative devices useful for stabilizing a beating heart are described, for example, in U.S. Pat. Nos. 5,894,843; 5,727,569; 5,836,311; and 5,865,730.

As beating heart procedures have evolved, new challenges have arisen in the design and engineering of the stabilization devices. The heart is typically accessed by way of a surgical incision such as a sternotomy or thoracotomy. Often one or more of the blocked or restricted coronary arteries are located a good distance away from the access incision requiring the stabilization device to traverse a longer and more tortuous path and engage the surface of the heart at somewhat difficult angular relationships or orientations. Under the most severe conditions, devices which operate to provide a mechanical compression force to stabilize the beating heart encounter difficulty maintaining mechanical traction against the surface of the heart. Similarly, devices which utilize vacuum to engage the heart have a great deal of difficulty creating and maintaining an effective seal against the moving surface of the heart.

Even when the beating heart has been effectively stabilized, the target coronary artery may be obscured by layers of fat or other tissue and is very difficult for the surgeon to see. Moreover, the stabilization devices may distort the tissue surrounding the coronary artery or the coronary artery itself such that the arteriotomy is maintained in an unfavorable presentation for completion of the anastomosis. For example, the coronary artery in the area of the arteriotomy may become excessively flattened, compressed or stretched in a manner that impedes the placement of sutures around the perimeter of the arteriotomy.

In view of the foregoing, it would be desirable to have methods and devices for stabilizing the beating heart that are capable of maintaining atraumatic engagement with the surface of the beating heart over a wider range of conditions and orientations. It would be further desirable to have stabilization methods and devices which provide for favorable presentation of the coronary artery.

SUMMARY OF THE INVENTION

The present invention will be primarily described for use in stabilizing the beating heart during a surgical procedure, but the invention is not limited thereto, and may be used in other surgical procedures.

The present invention is a tissue stabilizer having one or more stabilizer feet that may be adjusted or oriented to provide optimal engagement against the tissue to be stabilized or to provide an optimal presentation of a portion of the stabilized tissue. The present invention may also include a tissue stabilizer having one or more flexible or compressible seals to ensure a reliable seal against the target tissue and may also include a stabilizer foot having at least one portion which is adjustable relative to the remainder of the stabilizer foot.

One aspect of the present invention involves a device for stabilizing tissue within a patient's body comprising a base member, a first stabilizer foot extending outwardly from the base member and being rotatable relative to the base member about a first axis, and a second stabilizer foot extending outwardly from the base member and being rotatable relative to the base member about a second axis. Preferably, the first and second stabilizer feet are independently rotatable relative to the base member. In a preferred embodiment, the first axis and the second axis are substantially parallel.

The first and second stabilizer feet may each have hollow interiors defining first and second vacuum chambers each having at least one opening adapted to engage at least a portion of the tissue. The openings adapted to engage at least a portion of the tissue to be stabilized may have a raised seal around a perimeter thereof. In one variation the raised seal is made of a substantially rigid material. In other variations the raised seal is made of an elastomeric material or a compressible foam material.

The base member may comprise an interior chamber therein, the interior chamber of the base member being in fluid communication with the first and second vacuum chambers. The base member may comprise a front base portion and a rear base portion, the front base portion being sealingly affixed to the rear base portion. The device may also include a post having a distal end connected to the base member and a proximal end terminating in a ball-shaped member. A shaft may be provided having a socket at a distal end, the socket being operably engaged with the ball.

Another aspect of the present invention involves a device for stabilizing tissue within a patient's body having a base member and at least one stabilizer foot extending outwardly from the base member in a first direction, the stabilizer foot being rotatable relative to the base member about an axis of rotation which is oriented in substantially the same direction as the first direction. Preferably, the axis of rotation is at an angle of no more than about 25° to the first direction, more preferably, the axis of rotation is substantially parallel to the first direction.

In a preferred variation, the stabilizer foot has tissue engaging features adapted to engage an external surface of the tissue to be stabilized, the tissue engaging features being disposed at the bottom of the stabilizer foot. The tissue engaging features may comprise a vacuum chamber, preferably having a single opening for engaging the tissue to be stabilized, or may comprise a plurality of vacuum ports. The tissue engaging features may also comprise a textured surface, a perforated sheet, or a perforated sheet having projections extending outwardly therefrom. Preferably, the axis of rotation of the stabilizer foot is offset from the tissue engaging features, more preferably offset from and parallel to the tissue engaging features.

The stabilizer foot may have a hollow interior defining a vacuum chamber with a bottom opening adapted to engage at least a portion of the tissue. The stabilizer foot may also have a raised seal disposed around a perimeter of said opening, preferably around substantially the entire perimeter. The raised seal may be made from a rigid material, an elastomer, or a compressible foam. The vacuum chamber may have an inlet passage in fluid communication with a source of negative pressure. Preferably, the inlet passage is in fluid communication with an interior chamber within the base member. The base member may include an external fluid connection to supply negative pressure to the interior chamber of the base member.

Another aspect of the present invention involves a device for stabilizing a coronary artery on a patient's heart comprising a base member and a stabilizer foot for engaging a portion of the patient's heart. The base member has an interior chamber and at least a first bore, typically a cylindrical bore, having a first end in fluid communication with the interior chamber of the base member and a second end open to the exterior of the base member. The stabilizer foot has a substantially cylindrical fitting having a longitudinal axis, at least a portion of the fitting positioned within the bore and being rotatable within the bore about the longitudinal axis.

The stabilizer foot may have a hollow interior defining a vacuum chamber, the vacuum chamber having at least one chamber opening adapted to engage at least a portion of the heart. The fitting may further have a fluid passage having a first end in fluid communication with the interior chamber of the base member and a second end in fluid communication with the vacuum chamber of the stabilizer foot. A raised seal may be disposed substantially completely around the perimeter of the chamber opening. The raised seal may be rigid, compressible or flexible, preferably compressible or flexible. In a preferred embodiment, the raised seal has a durometer with a valve in the range of between about 35 Shore-A to about 100 Shore-A.

The stabilizer foot fitting may comprise a flange and further include an annular seal positioned adjacent the flange. Preferably, the annular seal is positioned between the flange and the base member. The annular seal is preferably an O-ring. The fitting includes at least one flexure having a free end and a raised portion extending radially from the free end. The raised portion preferably engages the first end of the first cylindrical bore to restrict movement of the fitting relative to the base member.

The tissue stabilizer may further include a second substantially cylindrical bore having a first end in fluid communication with the interior chamber of the base member and a second end open to the exterior of the base member. The tissue stabilizer may have a second stabilizer foot having a substantially cylindrical fitting having a longitudinal axis, at least a portion of the second stabilizer fitting positioned within the second bore and being rotatable within the second bore about the longitudinal axis of the fitting of the second stabilizer foot.

Another aspect of the present invention involves a stabilizer foot for use in engaging a portion of tissue within a patient's body which includes a first foot portion having at least one vacuum port, a second foot portion having at least one vacuum port, and at least one malleable member connecting the first foot portion to the second foot portion, whereby the orientation of the first foot portion can be adjusted relative to the second foot portion. Preferably, the first foot portion is a substantially rigid unitary member having at least two vacuum ports.

The first foot portion may have a fluid passage in fluid communication with each of the vacuum ports associated with the first foot portion and the second foot portion may have a fluid passage in fluid communication with each of the vacuum ports associated with the second foot portion. The malleable member may be a cylindrical tube having a first end, a second end, and a lumen extending therebetween, the lumen fluidly connecting the fluid passage of the first foot portion with the fluid passage of the second foot portion, preferably, the tube is made of stainless steel. In another variation, a flexible tube may be provided to connect the fluid passage of the first foot portion to the fluid passage of the second foot portion. The malleable member is then preferably offset from the flexible tube. Preferably, the stabilizer foot includes two malleable members offset from opposing sides of the flexible tube.

DETAILED DESCRIPTION

Figure 1A:
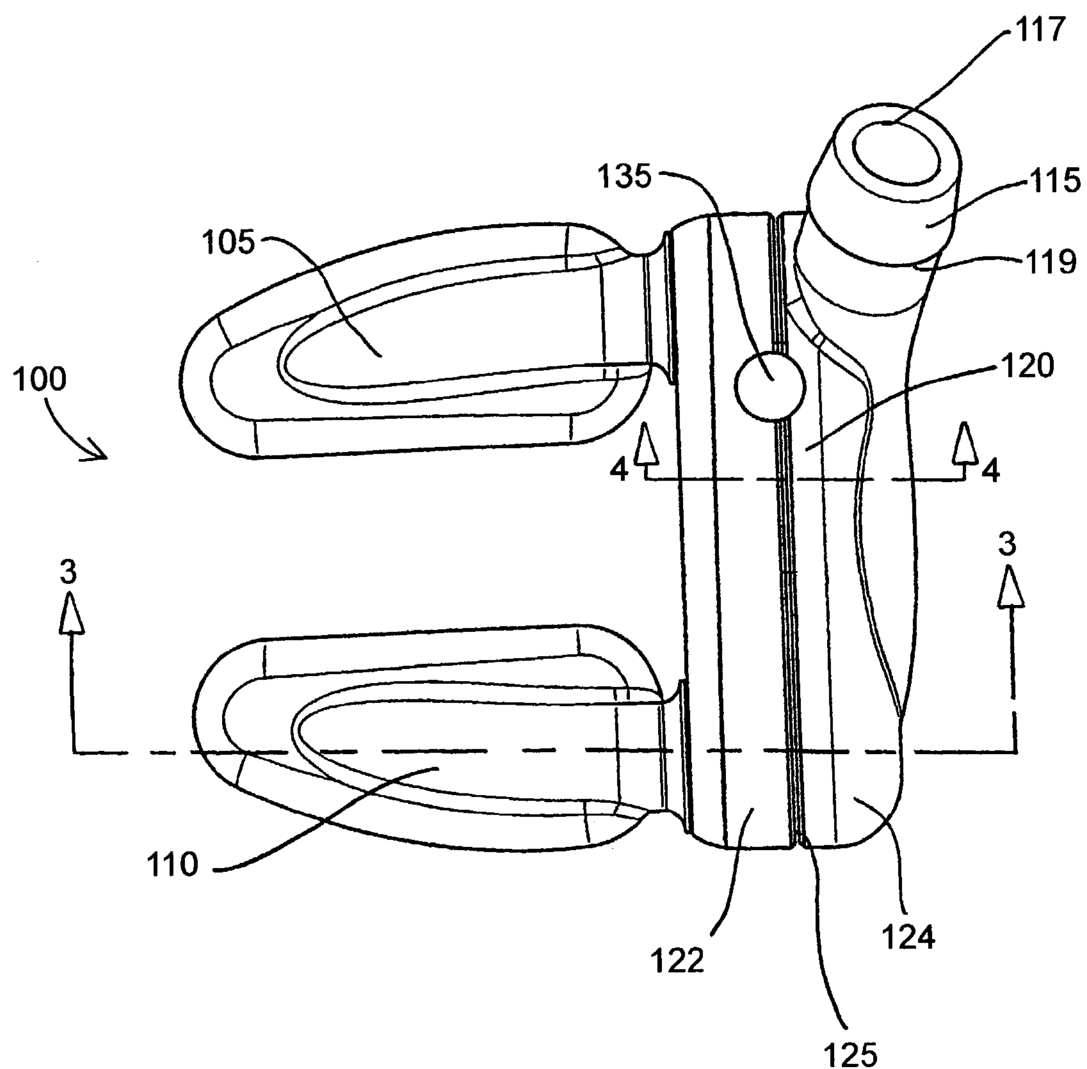
FIGS. 1A and 1B are top plan and top perspective views, respectively, of a tissue stabilizer constructed according to the principles of the present invention.
Figure 1B:
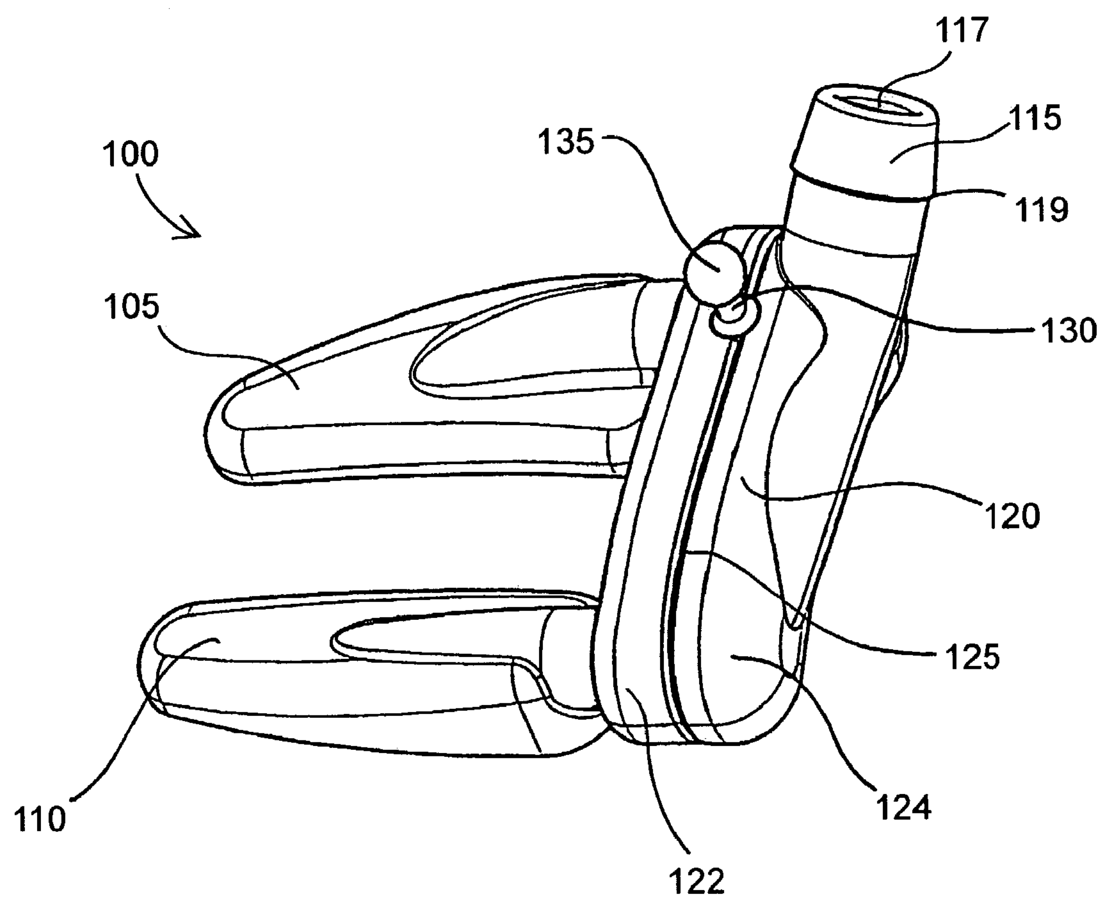

The present invention involves surgical instruments and methods for stabilizing tissue during a surgical operation. The devices described herein may be used in a wide variety of surgical applications that require a tissue structure to be stabilized or immobilized to provide a substantially stable and motionless surgical field on which a surgical procedure can be performed. By way of example only, the preferred embodiments described in detail below are directed to the stabilization of a portion of the heart to facilitate a surgical procedure on or within the heart, such as a coronary artery bypass graft (CABG) procedure.

Although the devices and methods of the present invention may have application in both conventional stopped-heart and beating heart procedures, they are preferably used to stabilize the beating heart during a CABG operation which has been specially developed to facilitate completion of an anastomosis, typically between a target coronary artery and a bypass graft or source artery, without requiring cardiac arrest and cardiopulmonary bypass.

A typical beating heart CABG procedure involves accessing the beating heart by way of a sternotomy, mini-sternotomy, thoracotomy, mini-thoracotomy, or other suitable access incision, positioning a tissue stabilizer on, around or adjacent a coronary artery to stabilize the coronary artery, creating an arteriotomy in the coronary artery, and anastomosing the bypass graft or source artery to the arteriotomy. Typically, the tissue stabilizer has a heart engaging member at one end for engaging the surface of the beating heart and is connected at the other end to a stationary object such as a sternal retractor, rib retractor, or other such stationary structure. Exemplar devices and methods for accessing the beating heart and mounting a stabilizer device are disclosed in co-pending U.S. patent application Ser. No. 09/305,810 titled "A SURGICAL RETRACTOR APPARATUS FOR OPERATING ON THE HEART THROUGH AN INCISION", the entirety of which is herein incorporated by reference.

The devices of the present invention involve tissue stabilizers which provide superior engagement with the surface of the heart. In preferred embodiments of the present invention, the tissue stabilizer may have one or more stabilizer feet which provide for adjustment of the orientation of the features which contact or engage the surface of the heart. In one instance, the orientation may be adjusted to ensure the engaging features will be properly aligned with the surface of the heart. In addition, once engaged with or connected to the heart, the orientation may be adjusted to yield an optimum presentation of the target coronary artery and, in particular, the location at which the anastomosis will be performed.

When the tissue stabilizer is configured to facilitate the use of negative pressure to engage the surface of the heart, the stabilizer feet may include one or more compliant or flexible seals to ensure that there will be no vacuum leaks between the stabilizer foot and the surface of the heart. To ensure that the engaging features provided on a stabilizer foot will closely approximate the surface of the beating heart under operating conditions, the stabilizer foot may have one or more portions which are adjustable relative to each other so that the stabilizer foot may be shaped according to the requirements of a particular surgical procedure or according to the specific anatomical features or characteristics of each individual patient.

Referring to the figures wherein like numerals indicate like elements, an exemplar tissue stabilizer is illustrated in FIGS. 1A-4. Tissue stabilizer 100 preferably has stabilizer feet 105 and 110 which typically engage the surface of the heart on opposite sides of a coronary artery. Tissue stabilizer 100 is typically positioned such that the coronary artery runs lengthwise in the space between stabilizer feet 105 and 110.

For beating heart procedures where the target vessel is occluded, tissue stabilizer 100 preferably has a construction that does not occlude or otherwise contact the vessel as stabilizer feet 105 and 110 are placed on opposite sides of the coronary vessel portion to be stabilized. Thus, stabilizer feet 105, 110 are spaced apart at a distance such that a coronary artery can be positioned therebetween. When stabilizer feet 105 and 110 are connected to a common base, the base may include a recessed or raised portion to ensure that the vessel is not contacted by the stabilizer. For example, manifold base 120, to which stabilizer feet 105 and 110 are attached, preferably has raised portion 126 under which the coronary vessel may pass without contact when stabilizer feet 105 and 110 are engaged to stabilize the heart in the vicinity of the coronary vessel.

Stabilizer feet 105 and 110 are connected to manifold base 120 which will typically have mounting or connecting features for operably attaching a suitable shaft or other such structure. Preferably manifold base 120 has a ball 135 extending therefrom. A shaft (not shown), preferably having a suitably constructed socket, may be provided to engage ball 135. The shaft may be used to position tissue stabilizer 100 at the desired location on the heart and may provide the necessary structure to hold the tissue stabilizer substantially motionless against the forces generated by the beating heart. Of course, the shaft or other appropriate connecting structure may be operably connected to the tissue stabilizer using any suitable connection which allows the desired maneuverability of the tissue stabilizer relative to the shaft. Suitable stabilizer shafts and their connections to a tissue stabilizer are described in co-pending U.S. patent application Ser. No. 08/931,158, titled "SURGICAL INSTRUMENTS AND PROCEDURES FOR STABILIZING THE BEATING HEART DURING CORONARY ARTERY BYPASS GRAFT SURGERY", and in EPO Application 97102789.1, the entirety of each are herein incorporated by reference.

Stabilization of the targeted tissue may be achieved by applying a localized compressive force to the heart through stabilizer feet 105 and 110 using an appropriate connecting structure attached to ball 135. In that case, the tissue contacting features on the bottom of stabilizer feet 105 and 110 are designed to have high friction against the surface of the heart, for example, by using a textured surface or the like. If desired, negative pressure or vacuum may be applied to stabilizer feet 105 and 110 so that the beating heart may be engaged or captured by the suction created within a vacuum chamber or a plurality of suction ports. With a localized portion of the beating heart so engaged against stabilizer feet 105 and 110, the heart portion may be rendered substantially motionless by fixing an attached shaft to a stationary object, such as a surgical retractor as described above.

Continuing to refer to FIGS. 1A-4, ball 135 is preferably connected to manifold base 120 by way of post 130. Ball 135 and post 130 may have any suitable construction which provides the necessary attachment of the stabilizing shaft or other stabilizing structure and which can withstand the loads required to stabilize the beating heart with minimal deflection. The ball and post may be integrally molded features on the manifold base itself or may be separate components mechanically secured to manifold base 120 using, for example, a threaded or snap-fit connection or the like.

When manifold base 120 is constructed of a plastic material, it may be desirable to fix post 130 to a relatively rigid support member to help spread stabilization loads transmitted through post 130 over a larger area of manifold base 120. Preferably, post 130 is rigidly attached to support member 155 which is made of a metal such as aluminum or stainless steel. In a preferred embodiment, support member 155 is secured within holding features such as cavities or pockets 156 and 158 formed in rear manifold portion 124 and front manifold portion 122, respectively. Support member 155 may be secured within pockets 156 and 158 by a simple interference fit as manifold portions 122 and 124 are urged into their final assembled positions or may be held in place using mechanical fasteners, adhesive, or suitable bonding or welding technique.

When the tissue stabilizer is configured to use vacuum stabilization or vacuum-assisted stabilization, manifold base 120 preferably has a fitting or the like to which a vacuum supply may be connected. In a preferred embodiment, manifold base 120 has inlet tube 115 having an inlet opening 117. Inlet tube 115 is preferably in fluid communication with a hollow space or chamber 134 formed within manifold base 120. Manifold base 120 and internal chamber 134 provides for convenient distribution of a single vacuum source connected to inlet tube 115 to multiple stabilizer feet fluid connections, in this case to stabilizer feet 105 and 110. Inlet tube 115 may have one or more barbs 119 to facilitate the secure and leak-free attachment of a length of flexible tubing (not shown) coming from a vacuum pump or other vacuum source (not shown) as is commonly known in the art. In an alternative embodiment, inlet tube 115 may be replaced with a generally cylindrical bore adapted to accept an O-ring sealed fitting forming a dynamically sealed rotating connection between the fitting and the manifold base similar in construction to the stabilizer foot connection described below with regard to FIG. 3.

For ease of manufacturing, manifold base 120 is preferably made in two or more portions and fixed together to form a sealed, hollow interior. In a preferred embodiment, manifold base 120 has front manifold portion 122 and rear manifold portion 124 which may be bonded together along bond line 125 as shown. The internal chamber 134 may reside primarily in either or both of front and rear manifold portions 122 and 124. To maximize the volume of internal chamber 134 for a given outer profile of manifold base 120, a portion of internal chamber 134 is formed in rear manifold portion 124 and one or more internal cavities 128 are included within front manifold portion 122.

The manifold portions are preferably injection molded and may be fixed together using standard mechanical fasteners, a snap fit construction, or any suitable adhesive, bonding, sealing, or welding technique compatible with the material of manifold base 120. To facilitate reliable bonding between the manifold portions, the manifold portions may have close fitting overlapping flanges. In a preferred embodiment, best illustrated in FIG. 3, rear manifold portion 124 has an inner flange 152 and front manifold portion 122 has an overlapping outer flange 154. This construction provides a particularly reliable sealed junction between front and rear manifold portions 122 and 124, especially when used in conjunction with a suitable gap-filling adhesive.

As mentioned above, stabilizer feet 105 and 110 are secured to manifold base 120. Stabilizer feet 105 and 110 may be fixed in place in any convenient manner and immovable relative to manifold base 120. More preferably, however, stabilizer feet 105 and 110 are moveable relative to manifold base 120. Most preferably, stabilizer feet 105 and 110 are independently moveable with respect to each other as well. This allows the tissue engaging features of the tissue stabilizer to be optimally adjusted with respect to the size and shape of the tissue to be stabilized and, once engaged and in operation, may also allow the stabilizer feet to be moved to optimize the presentation of the stabilized tissue, and more particularly the target coronary artery.

In a preferred embodiment, stabilizer feet 105 and 110 are connected to manifold base 120 in a manner which allows each foot to rotate relative to the manifold base 120. The axis about which the stabilizer feet 105 and 110 rotate may be in any orientation that provides the desired stabilizer feet orientation relative to the heart for optimum engagement or tissue presentation. Typically, the axis of rotation is oriented generally in the same direction as the direction stabilizer feet 105 and 110 extend from manifold base 120, although the axis of rotation and the direction the stabilizer feet extend may be offset from each other. Thus, the axis of rotation of the first stabilizer foot relative to the base member may be offset from the axis of rotation of the second stabilizer foot relative to the base member.

In a preferred embodiment, the axis of rotation is preferably at an angle of no more than about 25° with respect to the included plane or surface approximated by the features adapted to engage the tissue surface to be stabilized. More preferably, the axis of rotation for each stabilizer foot 105 and 110 is generally parallel to the features adapted to engage the tissue surface to be stabilized. When the tissue engaging features are curved to have a radius of a constant or varied radius or an otherwise non-planar, the axis of rotation is oriented as described above relative to a best-fit plane approximating the tissue engaging features or a central tangent plane. Most preferably, the axis of rotation for each stabilizer foot is also angled with respect to each other at an angle of no more than about 30°, and more typically the axis of rotation of stabilizer foot 105 is generally parallel to the axis of rotation of stabilizer foot 110.

Figure 3:
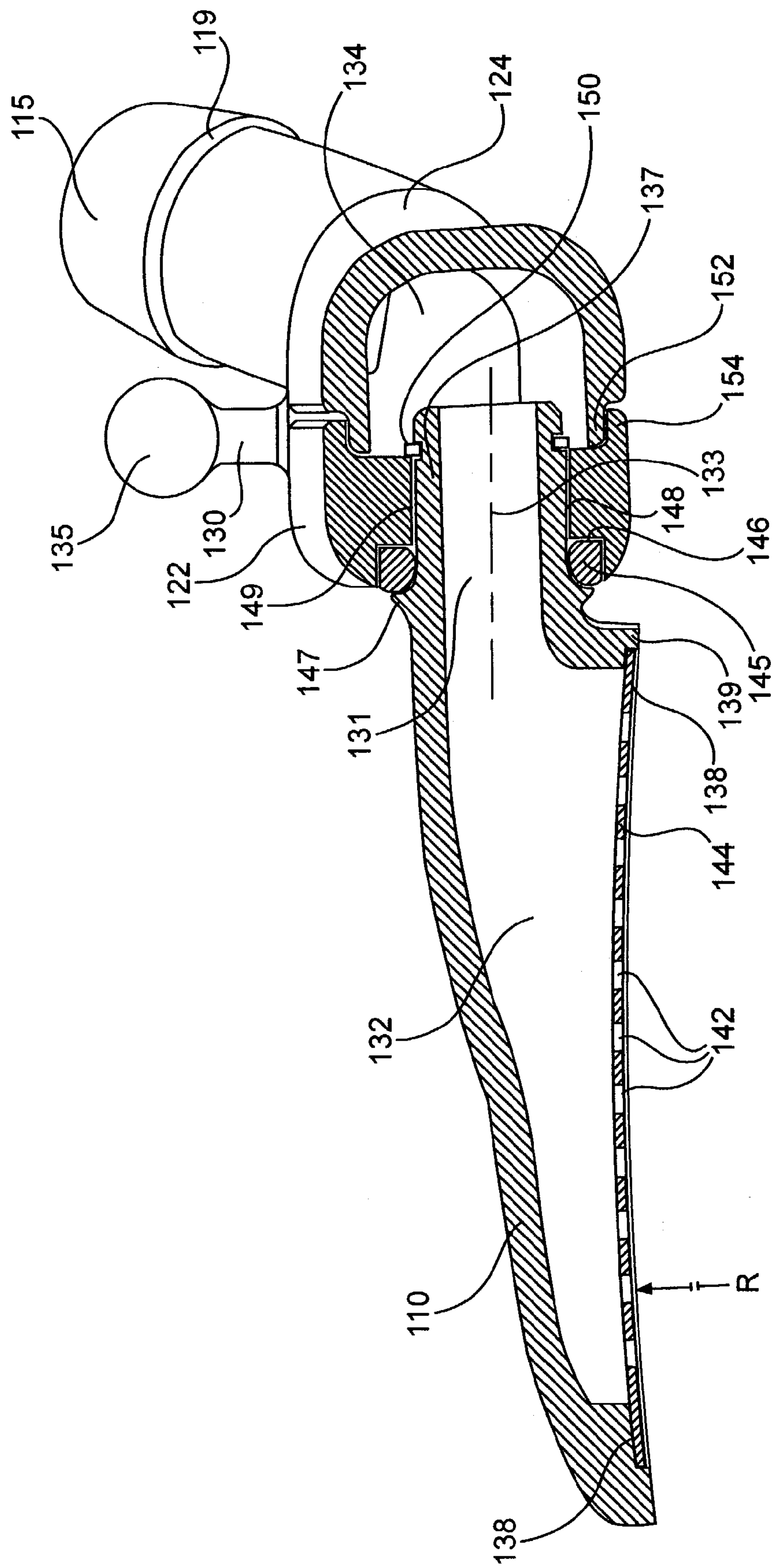
FIG. 3 is a cross-sectional view taken along line 3-3 as shown in FIG. 1A.
Figure 4:
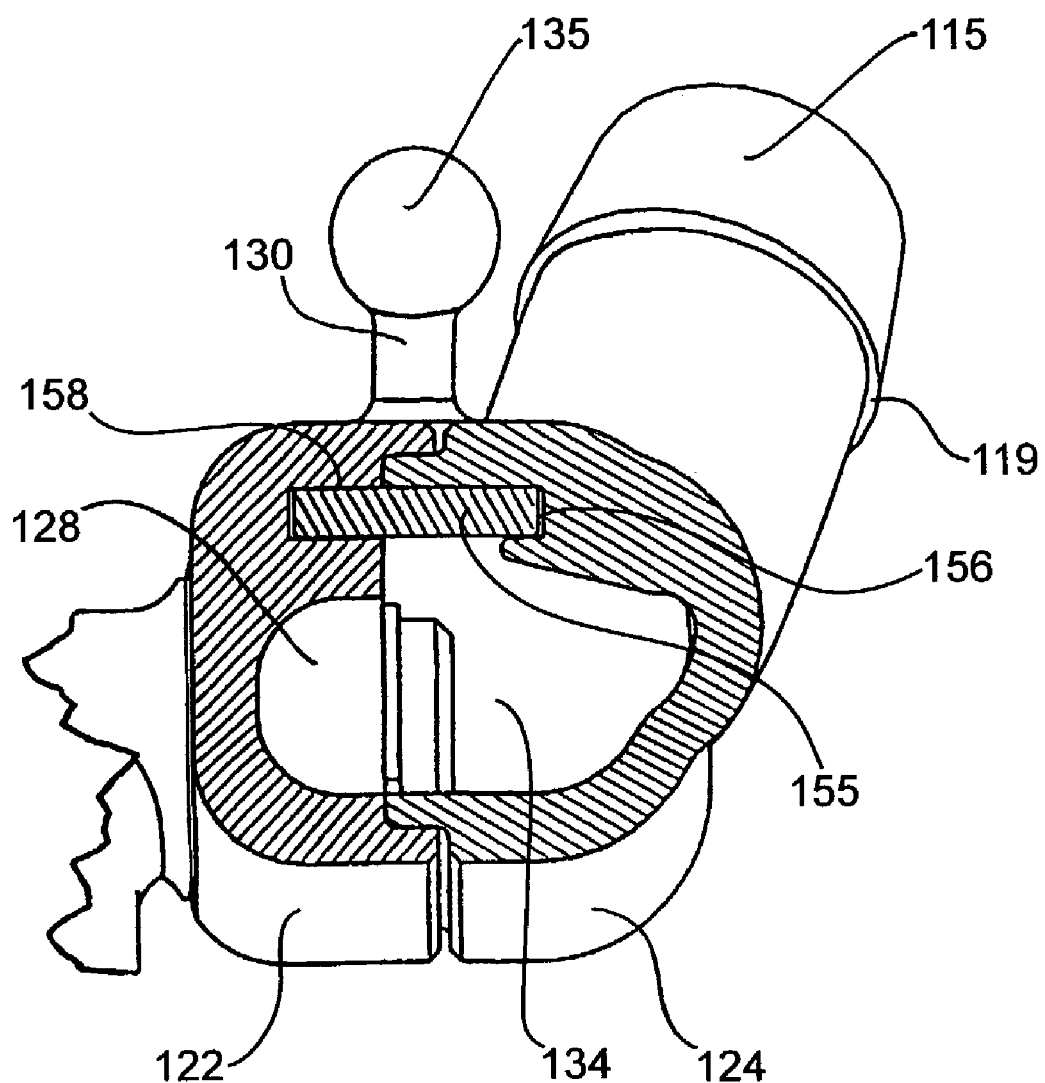
FIG. 4 is a cross-sectional view taken along line 4-4 as shown in FIG. 1A.

Referring to FIG. 3, a preferred stabilizer foot connection is illustrated with respect stabilizer foot 110. Manifold base 120, and more specifically front manifold portion 122, has a bore 149 extending through the exterior wall. Stabilizer foot 110 has an end portion or fitting 137 having an outside diameter 148 adapted to mate with bore 149 to allow fitting 137, and thus stabilizer foot 110, to rotate about central axis 133 of bore 149. In the configuration shown, central axis 133 is offset from the features which engage the tissue to be stabilized, in this case perforated screen 141. This offset facilitates improved vessel presentation as stabilizer feet 105 and 110 are rotated because, in addition to changing the overall orientation of the tissue engaging features, the eccentric relation of the tissue engagement features relative to the central axis moves the stabilizer feet together or apart as the stabilizer feet are rotated. This action allows the tissue and included coronary artery held between the stabilizer feet to be stretched or compressed as desired by rotating either or both of stabilizer feet 105 and 110 after they have become operably engaged with the tissue.

In a preferred embodiment of the present invention, the tissue stabilizer 100 is constructed to supply a negative pressure or vacuum to stabilizer feet 105 and 110 to assist in the engagement of the surface of the heart. Stabilizer feet 105 and 110 preferably have a hollow interior 132 to which a vacuum may be supplied through vacuum inlet 131 of fitting 137, vacuum chamber 134, and vacuum inlet tube 115, which are interconnected in a manner which does not allow any significant vacuum leaks. Collectively, the structures comprise a vacuum conducting chamber that communicates a negative pressure from a vacuum source to the surface of the beating heart. Vacuum inlet tube 131 may optionally have restriction or aperture (not shown) provided therein to restrict the amount of flow through vacuum inlet tube 131 when the sealed engagement against the tissue to be stabilized is broken. This allows vacuum chamber 134 of manifold base 120 to continue to provide sufficient vacuum to one stabilizer foot even when the engagement seal of the other stabilizer foot is compromised.

To allow vacuum to be communicated to the engagement features of stabilizer feet 105 and 110, the rotating connection between stabilizer feet 105 and 110 and manifold base 120 must be sealed to prevent any vacuum loss. This is preferably accomplished using an appropriate dynamic annular or shaft seal that seals between the stabilizer foot and manifold base 120 but yet allows for rotation of the stabilizer foot within bore 149 without incurring any vacuum loss. Preferably, a seal such as O-ring 145 positioned within an annual seal cavity 146 at the entrance of bore 149. The seal is captured and compressed within seal cavity 146 by cooperating annular seal flange 147 provided on stabilizer feet 105 and 110 as the stabilizer feet are urged into final position. Stabilizer feet 105 and 110 may be held in position by operation of an spring clip or e-clip 150 assembled to fitting 137 just beyond its exit of bore 149.

Hollow interior 132 is generally a closed chamber except for one or more openings for engaging the heart. As will be discussed in more detail below, the engagement opening or openings may be in the form of a perforated screen having a relatively large number of perforations or small holes which engage the surface of the heart, a single opening having a defined perimeter for sealing against the surface of the heart, or a plurality of individual suction pods each having a sealing perimeter.

Figure 2:
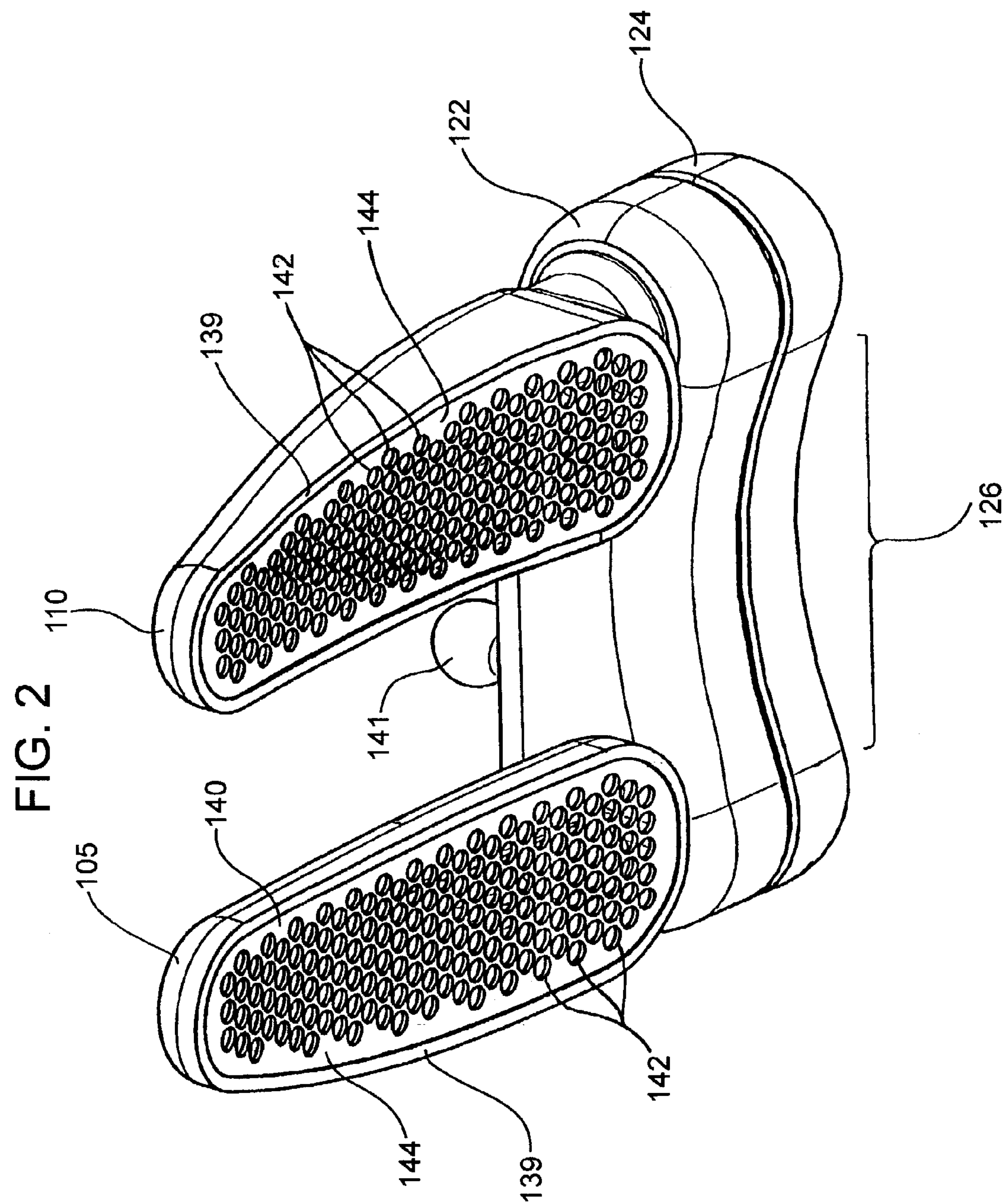
FIG. 2 is a bottom perspective view of the tissue stabilizer of FIGS. 1A and 1B.

Referring to FIGS. 2 and 3, stabilizer feet 105 and 110 include thin perforated sheets or screens 140 and 141, respectively which have a front surface 144 oriented to engage the surface of the heart. Perforated screens 140 and 141 are supported around their perimeter by a support step 138 which preferably has a raised perimeter edge or border 139. Perforated screens 140 and 141 are characterized as having a plurality of perforations or holes 142. Preferably, perforated screens 140 and 141 are fabricated to have a contour or shape which corresponds to the expected size and shape of the cardiac tissue to be stabilized. For example, perforated screen 140 and 141 may have a radius, R, which may be constant or variable.

As front surfaces 144 of perforated screens 140 and 141 are urged against the surface of the heart (or other tissue structure), the heart begins to contact front surface 144 around each perforation 142 and thus sealingly covering each perforation 142. As each perforation 142 is covered in this manner, the relatively small portion of tissue residing over each perforation 142 is subjected to the vacuum existing within hollow interior 132 and is accordingly sucked against, and even slightly into, perforation 142.

Because the total vacuum or suction force applied to the tissue is a function of the total tissue area exposed to vacuum, it is desirable for screens 141 and 142 to have the aggregate area of all the perforations as great as possible and still maintain the required structural integrity. In a preferred embodiment, the unperforated material between adjacent perforations is between about 0.015 inches (0.38 mm) and about 0.025 inches (0.635 mm) at its smallest point, most preferably about 0.02 inches (0.51 mm), and the diameter of the perforations are from about 0.06 inches (1.524 mm) to about 0.09 inches (2.286 mm).

Figure 8A:
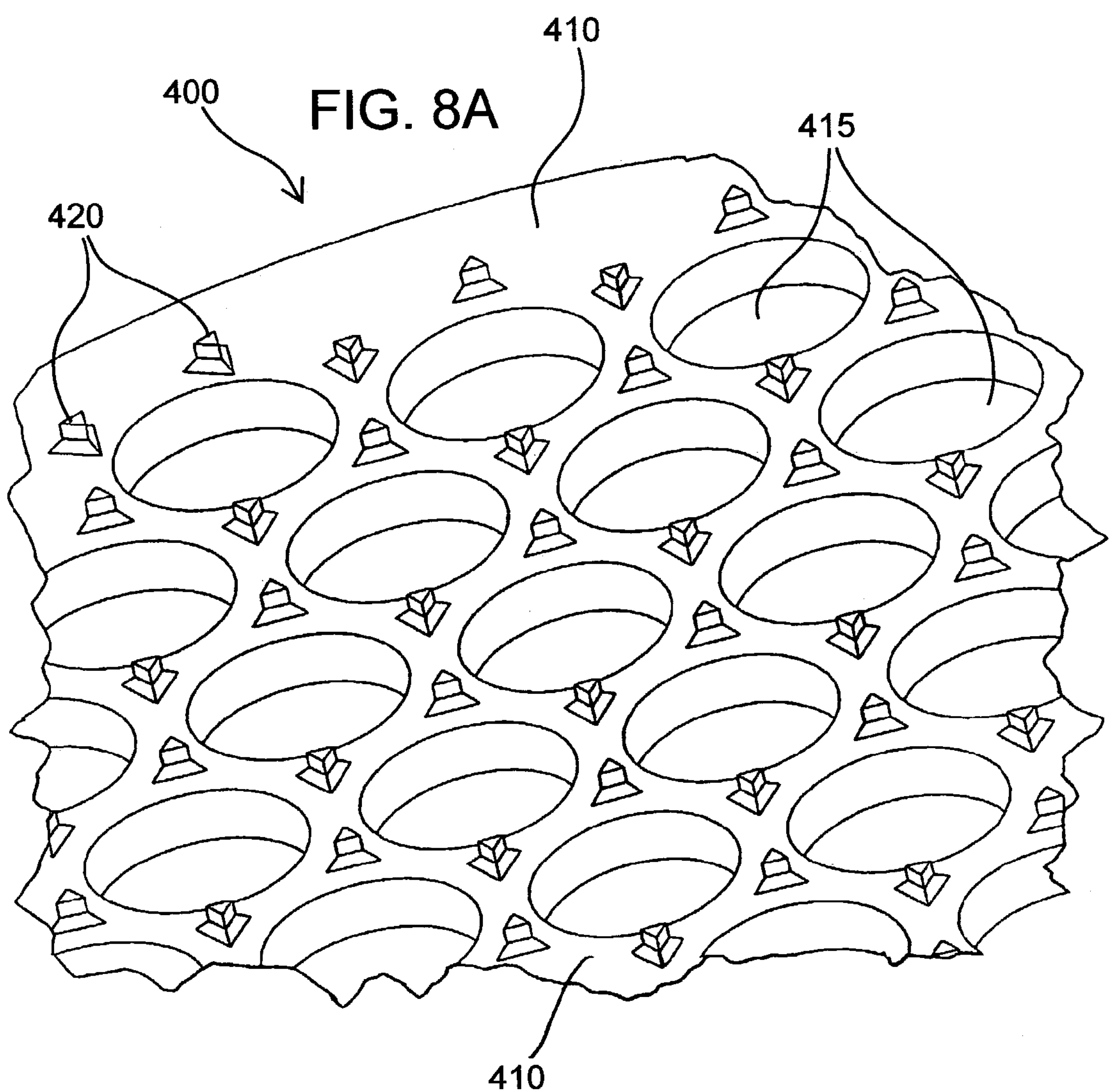
FIG. 8A is a magnified partial perspective view of a contacting surface of a preferred perforated screen for use in a tissue stabilizer.
Figure 8B:
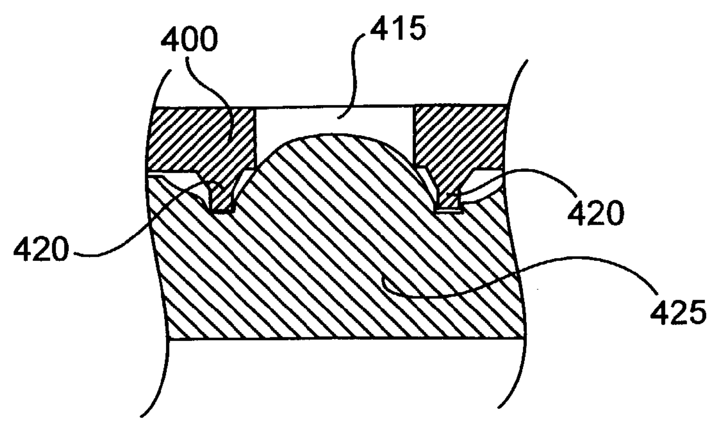
FIG. 8B is a partial cross-sectional view showing the perforated screen configuration of FIG. 8A engaged against a tissue structure.

A particularly advantageous configuration of front surface 144 includes a plurality of projections or protrusions disposed at a number of locations between the holes or perforations. FIGS. 8A and 8B illustrate a perforated member 400 having a front contact surface 410 which has a number of perforations or holes 415. The unperforated material of member 400 has a plurality of projections 420 extending outwardly from contact surface 410. In a preferred embodiment, a plurality of projections are generally equally spaced around each perforation 415. The projections may be formed, for example, by chemical machining or etching. Projections 420 operate to more aggressively bite or engage tissue structure 425 as it is urged into perforation 415 by operation of an applied vacuum.

Figure 5:
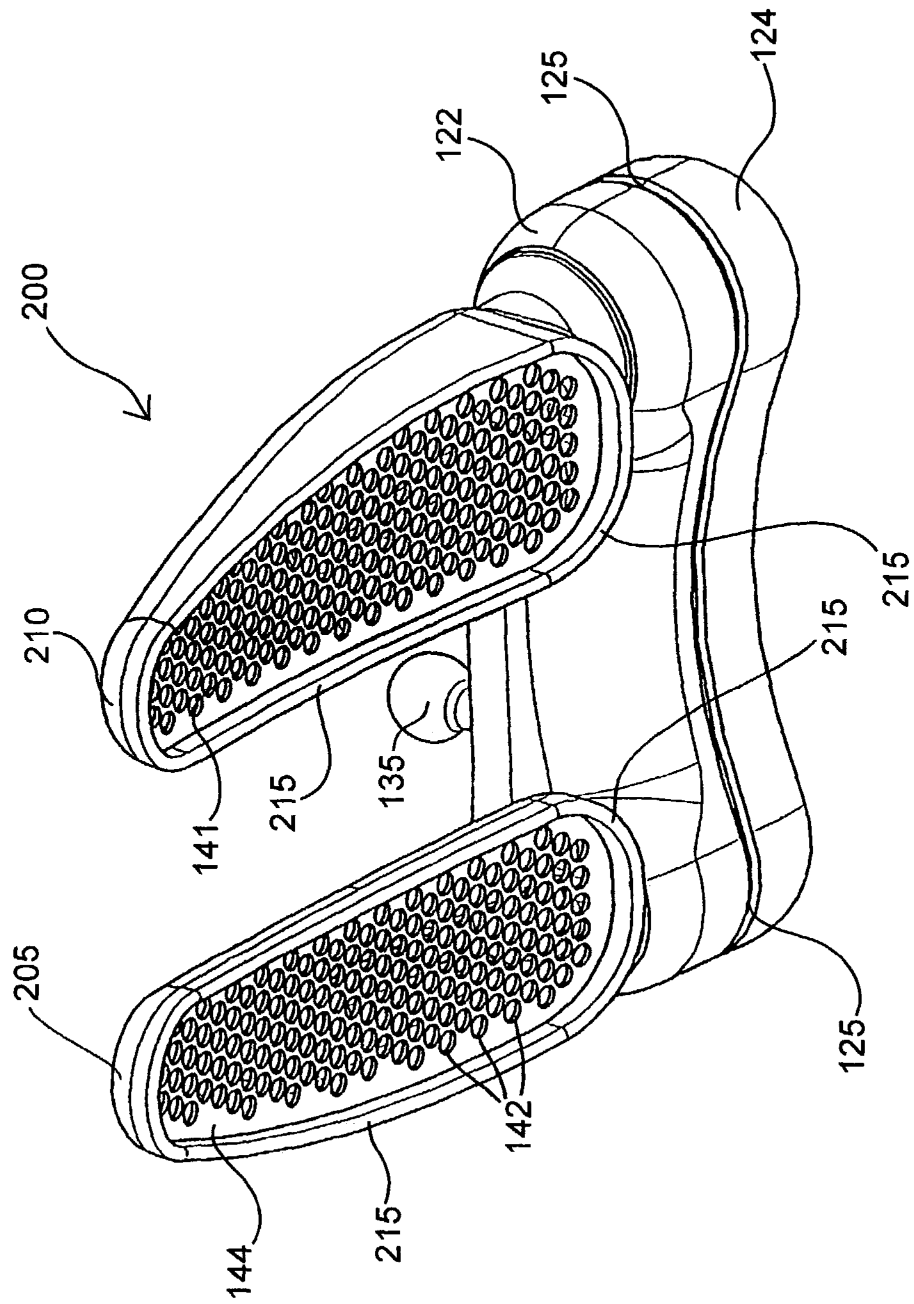
FIG. 5 is a bottom perspective view of an alternate construction of a tissue stabilizer according to the principles of the present invention.

In the embodiments shown in FIGS. 2 and 3, the outermost extending surface of border 139 is generally even or flush with front surface 144 of perforated screens 140 and 141. To maximize the total area of tissue exposed to vacuum, it may be desirable to have a raised border or perimeter which exposes and subjects all the tissue within its boundary to the negative pressure supplied through the interior of the stabilizer feet. FIG. 5 illustrates tissue stabilizer 200 having a perimeter sealing member 215 disposed at the bottom of each stabilizer foot 205 and 210. Perforated screens 140 and 141 are recessed from perimeter sealing member 215.

When perimeter sealing member 215 makes contact with the surface of the heart around substantially its entire perimeter, the portion of the heart tissue within the perimeter is subjected to the negative pressure existing within the hollow interior of stabilizer feet 205 and 210 and is urged into engagement with stabilizer feet 205 and 210. The negative or vacuum pressure may be sufficient to displace the portion heart tissue within the vacuum chamber created by perimeter sealing member 215 into forced contact with perforated screens 140 and 141. To further increase traction, perforated screens may optionally have projections as described above.

Figure 6:
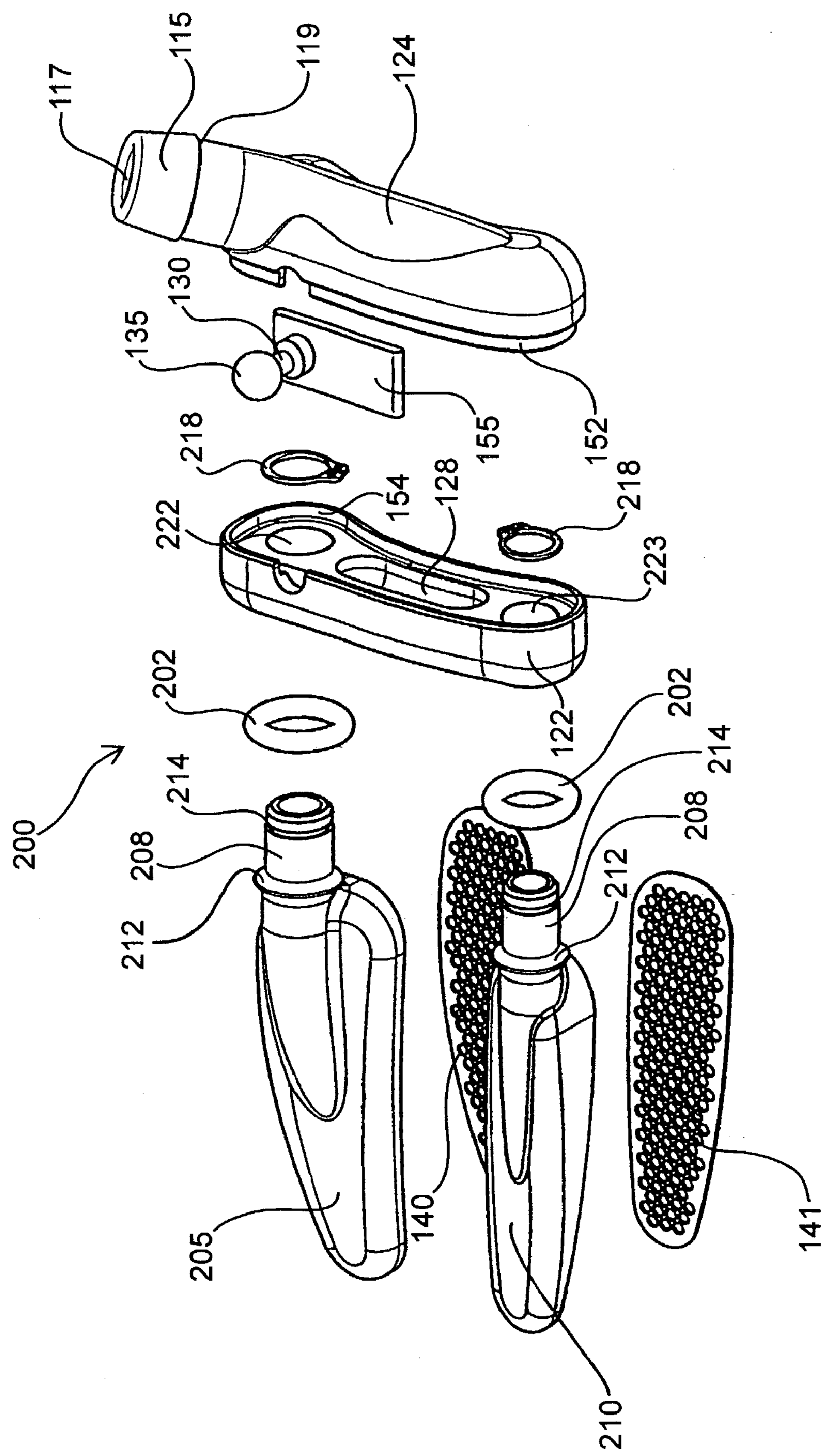
FIG. 6 is an exploded perspective view of a tissue stabilizer.

An exploded view of tissue stabilizer 200 is shown in FIG. 6. Front manifold portion 122 has first and second bores 222 and 223 for receiving tubular members or fittings 208 associated with stabilizer feet 205 and 210, respectively. Fittings

208 are preferably integrally molded features of stabilizer feet 205 and 210, but could alternatively be separate fittings secured to the stabilizer feet by way of, for example, a bonded, welded, or threaded connection. Fittings 208 have a flange 212 for retaining and compressing O-ring 202 within the seal cavity (not visible in this view) and groove 214 for receiving a external retaining ring, preferably of the spring type, e-type or the like. Fittings 208 preferably have a vacuum inlet opening 220 for communicating the negative pressure within manifold base 120 to the hollow interior region within stabilizer feet 205 and 210.

The multifunctional components of tissue stabilizer 200 allow for simple and convenient assembly. Stabilizer foot 205 may be assembled to front manifold portion 222 by installing O-ring 202 over fitting 208 and then installing fitting 208 through bore 222. Fitting 208 and stabilizer foot 205 is secured in place by securing an external retaining ring 218, into place within groove 214. The same procedure is then used to install stabilizer foot 210 to manifold portion 222. Post support member 155 is placed in the proper location between or within front and rear manifold portion 122 or 124 as the two manifold portions are brought together in the presence of an appropriate bonding agent or adhesive to make the assembly leak-free, air-tight, and permanent. Perforated screens 140 and 141 may be secured to stabilizer feet 205 and 210 at any convenient time before or after the assembly procedure just described.

Figure 7:
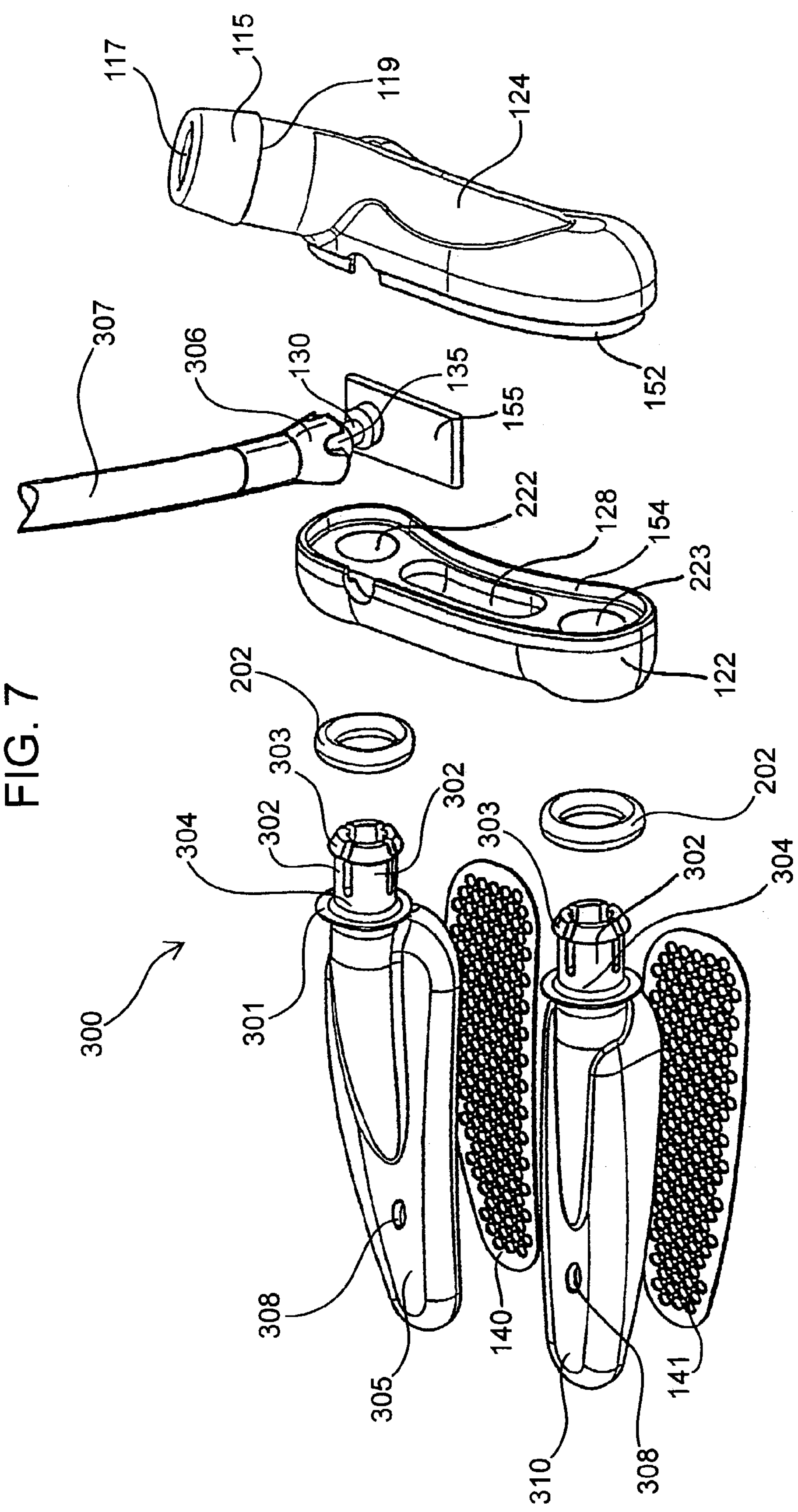
FIG. 7 is an exploded perspective view of an alternate construction of a tissue stabilizer.

Tissue stabilizer 300, shown in exploded view in FIG. 7, allows stabilizer feet 305 and 310 to be assembled to front manifold portion 122 using a simple snap-fit construction instead of an external retaining ring. In this variation, the fitting portions of stabilizer feet 305 and 310 include a seal flange 310, an uninterrupted base portion 304 and a number of flexures 302 having raised end features 303. Flexures 302 allow raised features 303 to flex inwardly so that they fit through bore 222 and 223 and then flex outwardly as they exit bores 222 and 223, thus becoming locked in place.

Tissue stabilizer 300 may be assembled using the same basic procedure as described above with reference to tissue stabilizer 200. In addition, however, because there is no retaining feature to be installed to the fitting portion after placement through bores 222 and/or 223, the front and rear manifold portions 122 and 124 can be fully assembled and leak tested (if desired) before stabilizer feet 305 and 310 are installed. Thus, post support member 155 is positioned in place in or between front and rear manifold portions 122 and 124 as the two manifold portions are brought together in the presence of an appropriate bonding agent or adhesive to secure the manifold base assembly together. An O-ring 202 is then placed over uninterrupted portion 304 adjacent flange 310 and raised features 303 on flexures 302 are urged through bore 222 or 223 until it exits the bore and snaps open and into place, thus fixing stabilizer foot 305 or 310 to the assembled manifold base.

Tissue stabilizer 300 shows a variation in which a stabilizer shaft 307 is preinstalled on ball 135. Stabilizer shaft 307 has a socket housing 306 which is permanently operably attached to ball 135. The ball 135 and post 130 is dropped into housing 306 from a distal direction prior to fixing shaft 307 thereto. Post support member 155 is then fixed to the proximal end of post 130, rendering the assembly essentially inseparable. This eliminates any possibility of accidental separation of the stabilizer foot from the stabilizer shaft.

To gain the advantage of stabilizer feet having different constructions for different procedures or patients, the foregoing design allows the desired stabilizer feet to simply be snapped into place within bores 222 and 223, for example, after a clinical determination has been made regarding what size, type, etc. of stabilizer feet will be presently required. Once snapped into place, stabilizer feet 305 and 310 may be rotated to obtain the desired orientation of each foot to provide maximum stabilization based on the clinical situation presented by an individual patient.

Stabilizer feet 305 and 310, or any of the other stabilizer feet described herein, may be provided with additional features to facilitate adjustment of stabilizer feet 305 and 310 after engagement with the tissue to be stabilized. The features may be any holes, lever, protrusion, projection, or other suitable feature that allows the stabilizer feet to be easily manipulated during use. Since it is desirable for the device to have an unobstructingly low-profile, especially in the area of the stabilizer feet, the adjustment features are preferably one or more blind holes 308 adapted to receive a blunt instrument for manipulating the orientation of stabilizer feet 305 and 310. Alternatively, a hex or nut-shaped feature could be added to each stabilizer foot distal of the seal flange for use with an appropriately sized wrench or the like to rotate the stabilizer feet.

Perimeter sealing member 215 may have a variety of constructions. Sealing member 215 may simply be an integral extension of the stabilizer foot material. In that instance, sealing member 215 will typically be a relatively hard polymer or plastic material. Sealing member 215 may also be a relatively soft elastomer which is attached to or over-molded on stabilizer feet 205 and 210. Sealing member 215 may also be constructed of a compressible foam material, preferably a closed cell foam. The elastomer or foam materials will preferably compress, deflect or otherwise yield somewhat as the stabilizer feet become engaged with the irregular surface of the heart. When sealing member 215 is constructed of an elastomer or foam material, it will preferably have a durometer hardness in the range from about 35 Shore-A to about 100 Shore-A depending on the geometrical configuration of sealing member 215.

Figure 9A:
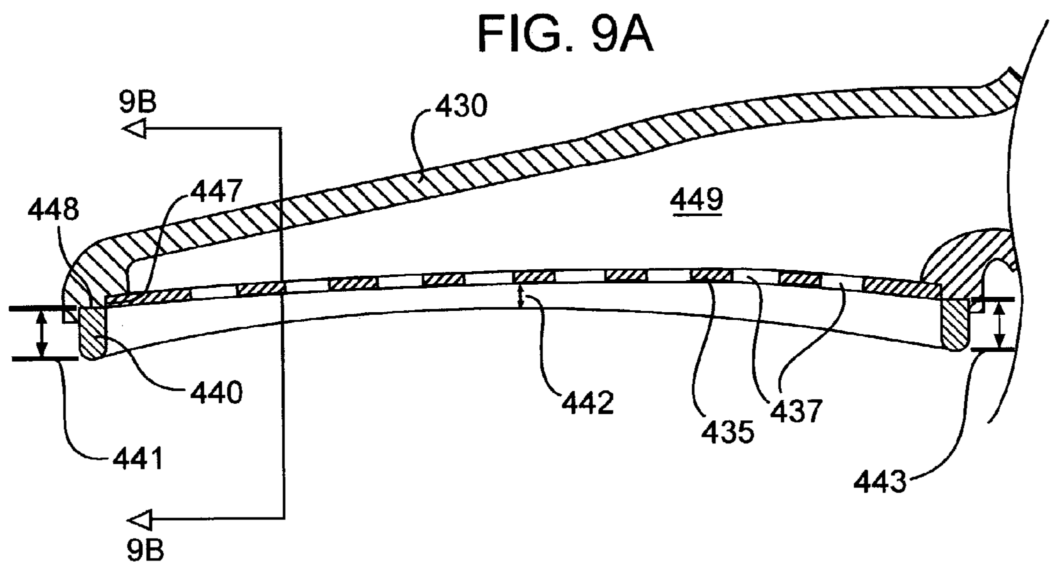
FIGS. 9A and 9B are partial cross-sectional views of a tissue stabilizer foot having a perimeter seal.
Figure 9B:
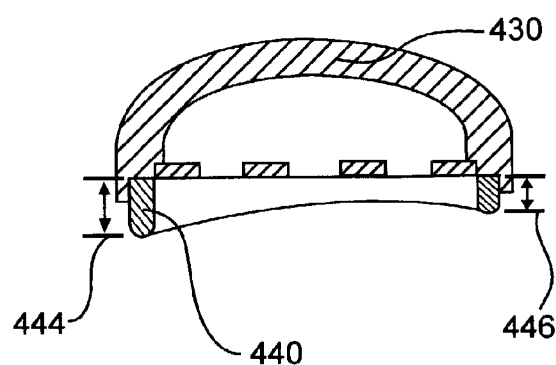

In a preferred embodiment, the perimeter seal has a variable thickness around its perimeter to provide a more reliable seal against the curvature of the surface of the heart, especially when the heart continues to beat during the procedure. FIGS. 9A and 9B show a portion of a stabilizer foot 430 having a perimeter seal 440 with a variable height or thickness around its perimeter. Similar to the previously discussed configurations, stabilizer foot 430 has a hollow interior 449 to which a negative pressure is communicated. Perforated screen 435 has a plurality of holes or perforations 437 and is mounted in position on step feature 447 within stabilizer foot 430. Perimeter seal 440 is mounted at or near the bottom of stabilizer foot 430, and is preferably retained within a groove or step 448.

The height that perimeter seal 440 extends from the bottom of stabilizer foot 430, typically varies at different locations around the perimeter of perimeter seal 440. For example, the tip height 441 and rear height 443 is generally greater than midpoint height 442 along either side of the stabilizer foot. In addition, height 446 of perimeter seal 440 along the inside of stabilizer foot 430, that is the side closest to the target artery, is generally less that the outside height 444 at a corresponding location along the stabilizer foot 430.

The variable height results in a contoured shape of perimeter seal 440 which tends to remain sealed against the heart when the heart expands and contracts as it beats to pump blood. In a preferred embodiment perimeter seal 440 is made from an elastomer, a closed-cell foam, or other flexible or compressible material to further optimize the ability of stabilizer foot to maintain its seal on the tissue to be stabilized. If the seal is broken or otherwise compromised, the stabilizer foot may disengage from the surface of the heart, adversely affecting stabilization. Seal 440 may be fixed to the stabilizer foot using an adhesive or bonding agent or may be made integral with the stabilizer foot using an injection over-molding process wherein seal 440 is molded over the stabilizer foot.

Figure 10:
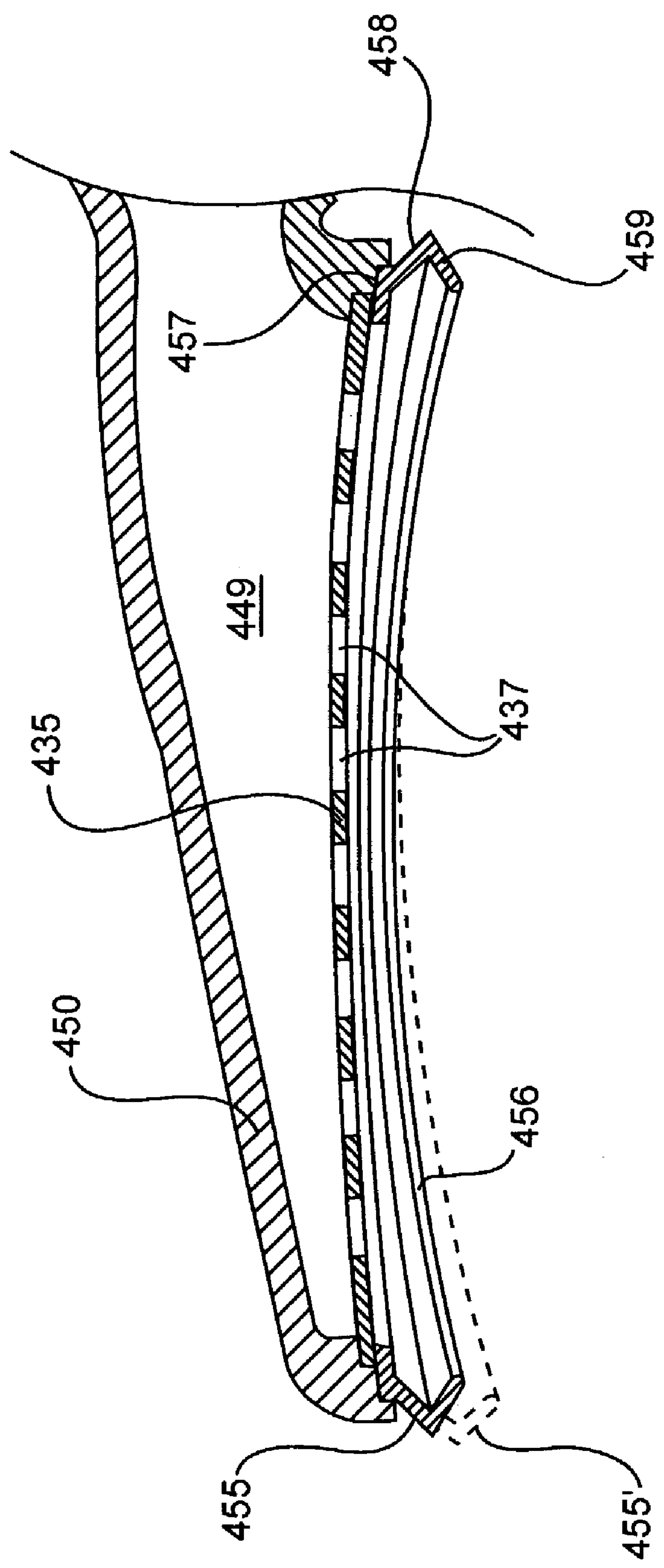
FIG. 10 is a partial cross-sectional view of a tissue stabilizer foot having an alternate perimeter seal.

Another seal variation is illustrated with reference to stabilizer foot 450, a portion of which is shown in FIG. 10. Stabilizer foot 450 again has a hollow interior 449 and a perforated screen 435 having perforations or holes 437. In this variation, stabilizer foot 450 has a flexible seal 455 having first and second legs 458 and 459 disposed in an angular relationship which operates as a highly flexible joint allowing perimeter edge 456 to move relatively freely towards and away from the bottom of stabilizer foot 450 as required to effectuate a reliable seal against the surface of the tissue to be stabilized. For example, if the tissue under vacuum engagement with stabilizer foot 450 contracts and moves away from the tip of stabilizer foot 450, flexible seal 455 can easily follow the movement to a new extended position 455' without the seal being broken.

Flexible seal 455 is preferably made from a medical grade elastomeric material such as silicone, urethane rubber, neoprene, nitrile rubber, hytrel, kraton, or other suitable material. Flexible seal 455 may be separately formed and later attached to stabilizer foot 450 or may be integrally over-molded onto stabilizer foot 450. For secure attachment to stabilizer foot 450, flexible seal 455 may optionally be provided with seal base portion 457.

Figure 11:
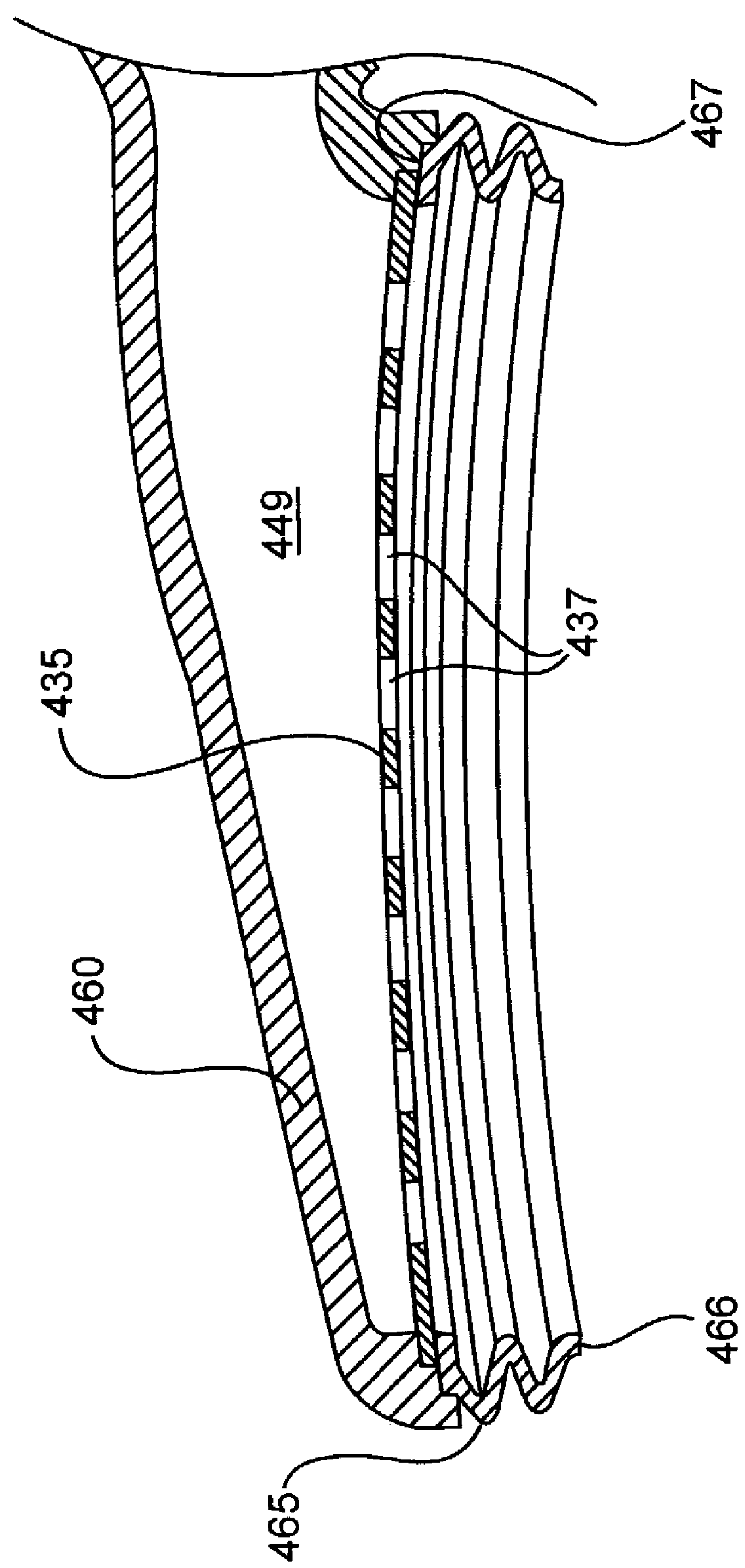
FIG. 11 is a partial cross-section view of a tissue stabilizer foot having an alternate perimeter seal.

If greater extension of the flexible seal's perimeter sealing edge away from the stabilizer foot is required, a seal having a greater number of flexible legs in a bellows or accordion type arrangement is employed. Referring to FIG. 11, stabilizer foot 460 has flexible seal 465 having continuously connected alternating flexible legs in the form of a bellows. Flexible seal 465 may include a base 467 to facilitate attachment to the bottom of stabilizer foot 460 and has a perimeter edge 466 to effectuate a reliable seal against the surface of the tissue to be stabilized. This type of seal generally compresses to a relatively solid, stable structure as the stabilizer foot is urged against the surface of the tissue, has a the ability to follow moving tissue over a relatively long travel if required, and yet occupies only a very small amount of space around the perimeter of the stabilizer foot.

Figure 12:
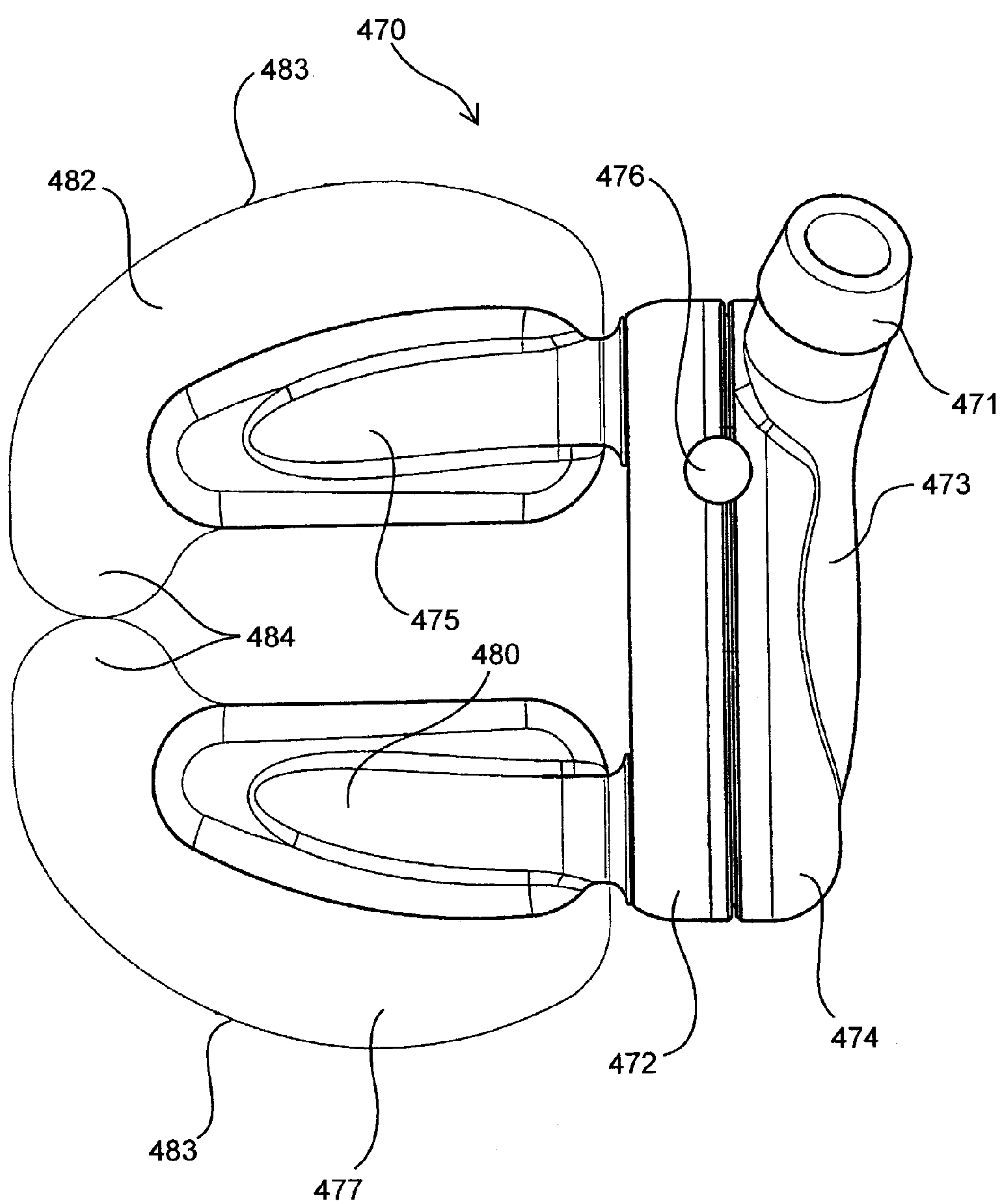
FIG. 12 is a top plan view of a tissue stabilizer having an alternative perimeter seal.
Figure 13A:
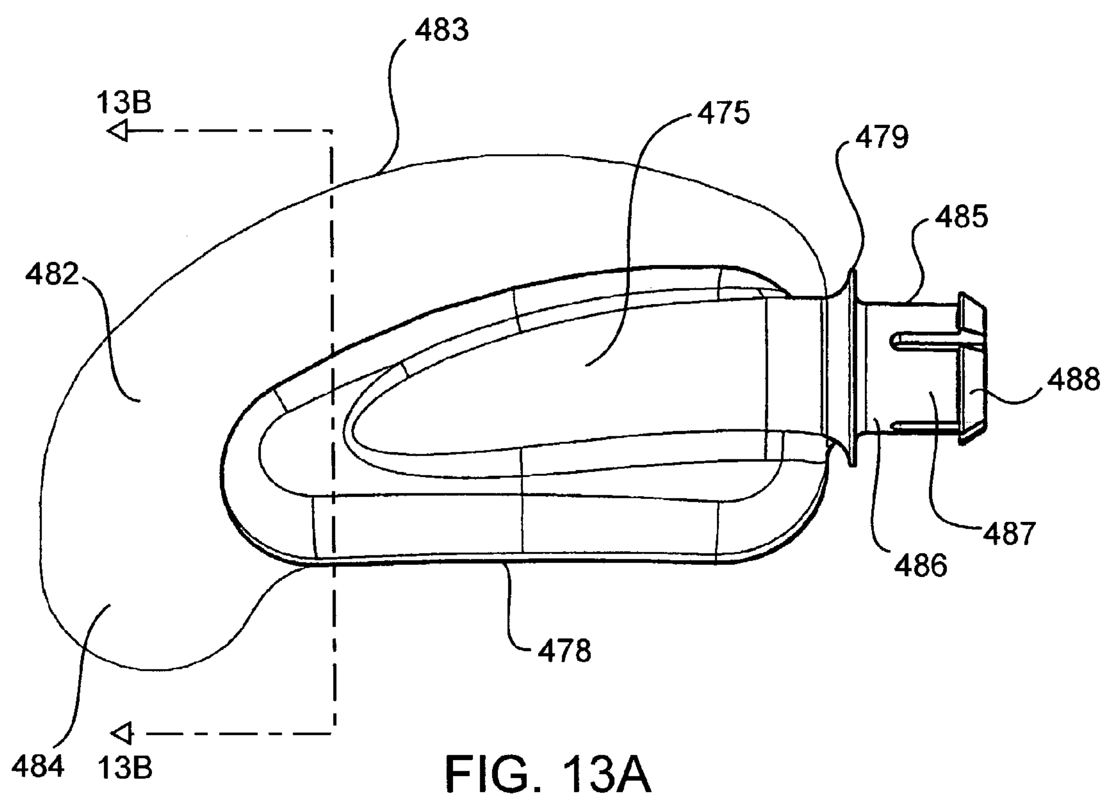
FIG. 13A is a top perspective view of the stabilizer foot of FIG. 12.
Figure 13B:
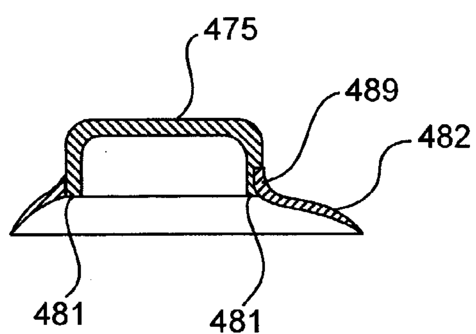
FIG. 13B is a cross-sectional view taken along line 13B-13B as shown in FIG. 13A.

Another flexible seal arrangement is illustrated in FIGS. 12-13B with reference to tissue stabilizer 470. Tissue stabilizer 470 has a manifold base 473 comprised of front manifold portion 472, rear manifold portion 474 having vacuum inlet tube 471, and ball 476 to which a stabilizing shaft may be attached. Stabilizer feet 475 and 480 may be attached to stabilizer base 473 in any of the ways discussed above. Most preferably, stabilizer feet 475 and 480 have a fitting portion 485 which includes an uninterrupted cylindrical portion 486, one or more flexures 487 each having raised features 488 that provide a positive snap-fit joint in cooperation within cylindrical bores formed in front manifold portion 472 as described in detail above. Preferably, fitting 485 has a flange 479 for retaining and compressing a shaft seal or the like.

Stabilizer feet 475 and 480 have attached thereto flexible seals 482 and 477, respectively. Flexible seals 477 and 482 may extend completely around the perimeter of stabilizer feet 480 and 475. More preferably, stabilizer feet 475 and 480 have at least one portion of its perimeter having a flexible seal and at least one portion without a flexible seal. According to this variation of the present invention, the stabilizer feet 475 and 480 are primarily sealed against the target tissue by operation of their own perimeter edge 481. Flexible seals 482 and 477 are provided generally outside of perimeter edge 481 to provide a form of secondary or back-up seal in the event the seal at perimeter edge 481 becomes compromised as a result of misalignment or movement of the tissue. Flexible seals 477 and 482 are preferably sufficiently flexible to remain in contact with the movements of the beating heart so that when the seal breaks along 481 perimeter edge the vacuum loss is contained within flexible seal 482 or 477. This containment typically allows the comprised area of perimeter edge 481 to become re-engaged against the tissue without significant vacuum loss.

After engagement and stabilization of the beating heart, the vacuum seal formed at the perimeter edge of the stabilizer feet may be most likely to break at the tip region or along the outside edge of the stabilizer foot as the heart contracts away from the site of stabilization. In such circumstances, flexible seals 477 and 482 need only be associated with these problem areas, leaving inside perimeter portion 478 and the space between stabilizer feet 475 and 480 open to avoid obstructing the surgical field of the anastomosis. Flexible seals 477 and 482 have a contoured outer periphery 483 which may be a relatively large distance away from the outer extents of the stabilizer feet 475 and 480 and may include extended tip portions 484. Flexible seals 477 and 482 preferably have a top portion for attaching to the stabilizer feet about the perimeter edge 481. Flexible seals 477 and 482 may be fixed in place using an adhesive or bonding agent or may be integrally over-molded as part of stabilizer feet 475 and 480.

Another way to prevent a complete loss of engagement and stabilization of the target tissue due to a compromised perimeter seal resulting from misalignment of the stabilizer feet or movement of the target tissue to be stabilized, is to partition the vacuum chamber within the stabilizer feet into a plurality of chambers connected to the vacuum source through only a small aperture. In that way, a vacuum leak at a single location will result in a reduced ability to maintain engagement of that partitioned section only and will not immediately compromise the engagement of the entire stabilizer foot. Of course, it may be desirable to combine any one of the flexible seals described above with partitioning to further increase the reliability of the stabilizer foot seal against the tissue structure to be stabilized.

Figure 14:
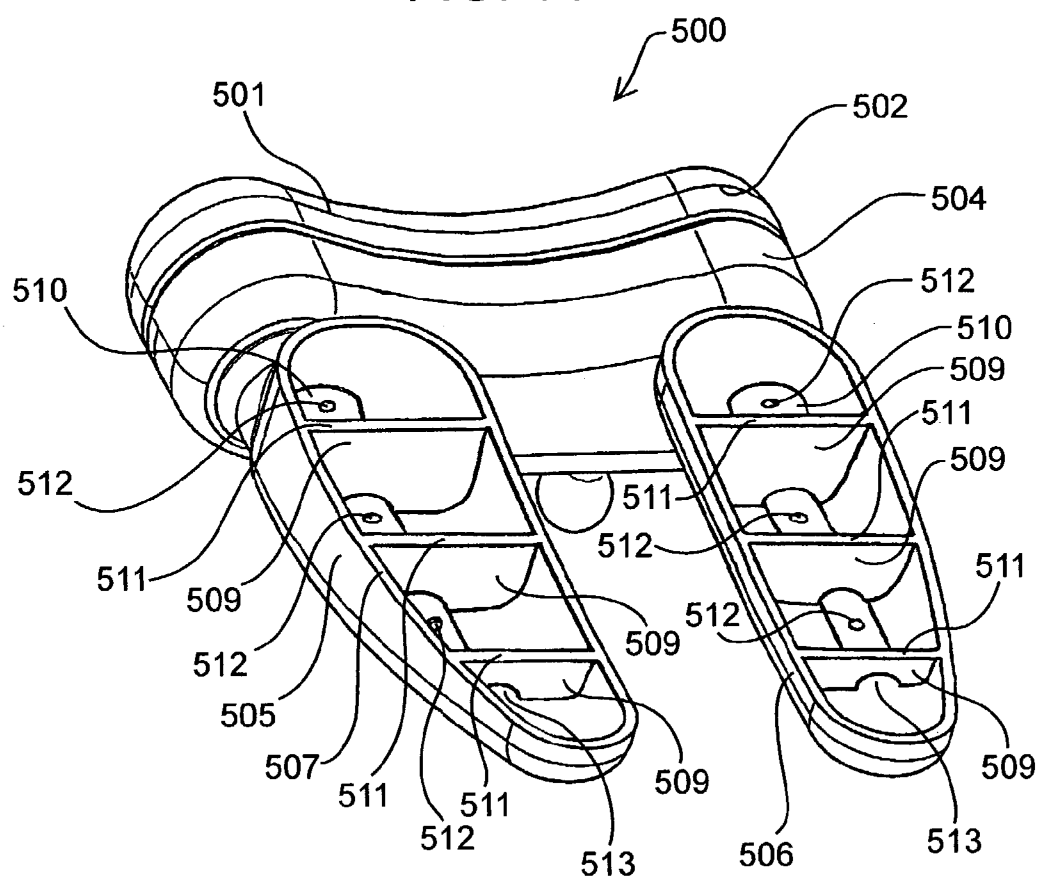
FIG. 14 is a bottom perspective view of an alternate construction of a tissue stabilizer according to the principles of the present invention.
Figure 15:
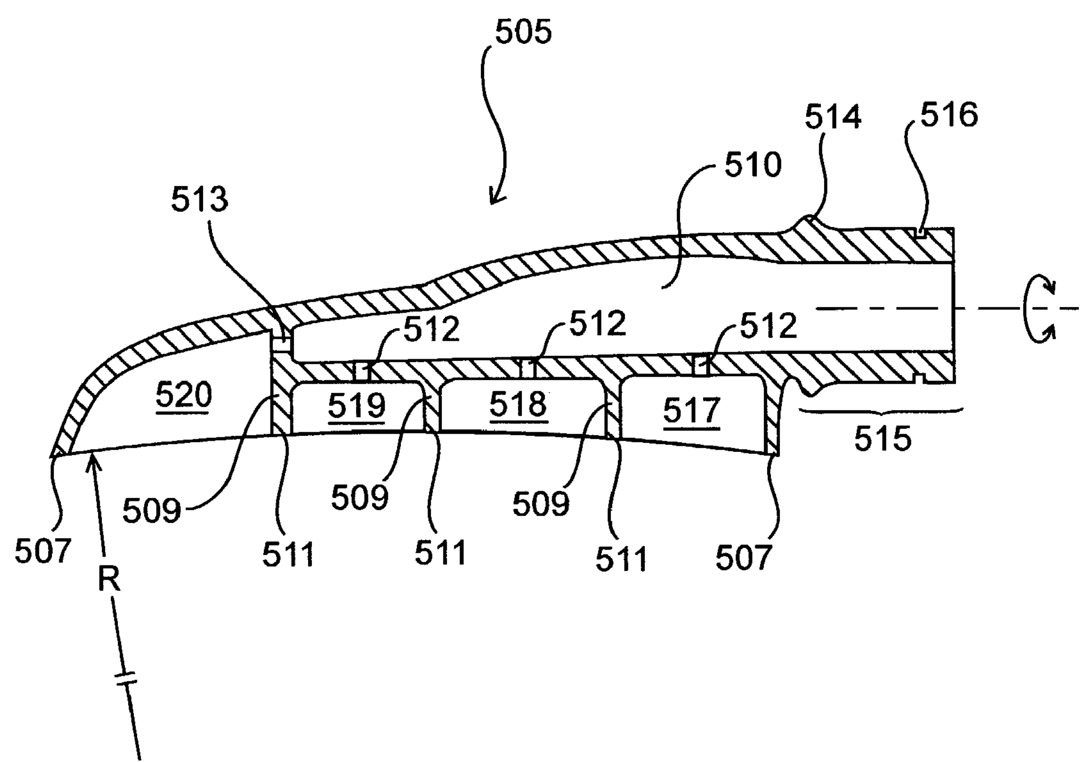
FIG. 15 is a cross-sectional view of one of the stabilizer feet of FIG. 14.

A tissue stabilizer embodiment having stabilizer feet with a partitioned vacuum chamber is illustrated in FIGS. 14 and 15. Tissue stabilizer 500 has a manifold base 501, preferably having front and rear manifold portions 504 and 502, to which first and second stabilizer feet 505 and 506 are attached. First and second stabilizer feet 505 and 506 have perimeter seal edges 507 and 508 which generally define the extents of the vacuum chambers for each stabilizer foot. One or more partitions 509, each having a sealing edge 511, are provided to divide stabilizer feet 505 and 506 into two or more vacuum subchambers. By way of example only, stabilizer feet 505 and 506 have partitions 509 which divide the vacuum space into first, second, third, and fourth vacuum subchambers 517, 518, 519, and 520, respectively.

Vacuum feed tube 510 is provided along the interior of stabilizer feet 505 and 506 to communicate the negative pressure from within the manifold base to each of subchambers 517, 518, 519, and 520. Vacuum feed tube 510 preferably has a side opening or aperture 512 within each of subchambers 517, 518, and 519. Vacuum feed tube 510 may have an end opening or aperture 513 within subchamber 520. The apertures 512 and 513 facilitate the separate communication of negative pressure to each vacuum subchamber and are preferably sized such that when one subchamber encounters a vacuum leak, the aperture is restricted enough so that the vacuum in the other subchambers can be maintained by the vacuum source.

Stabilizer feet 505 and 506 are preferably rotatable with respect to manifold base 501 as discussed at length above. For example, stabilizer feet 505 and 506 may have a fitting portion 515 which is preferably cylindrical to cooperate with a mating bore provided in manifold base 501. Fitting portion 515 may have a flange 514 for retaining a shaft seal and a groove for receiving an external retaining ring to secure fitting portion 515 within manifold base 501. The bottom of stabilizer feet 505 and 506 may have a contoured shape having a variable or fixed radius, R. A flexible seal may optionally be included along one or all of sealing edges 507, 508, and 511.

A partitioned vacuum chamber as described above maximizes the area exposed to negative pressure for a particular size of stabilizer foot. That is, the ratio of the surface area exposed to negative pressure divided by the total surface area included with the boundary at the bottom of the stabilizer foot is maximized by the partitioned chamber configuration just described. In another embodiment, although less efficient in that regard, rotatable stabilizer feet can be constructed to have a number of individual vacuum ports or pods.

Figure 16:
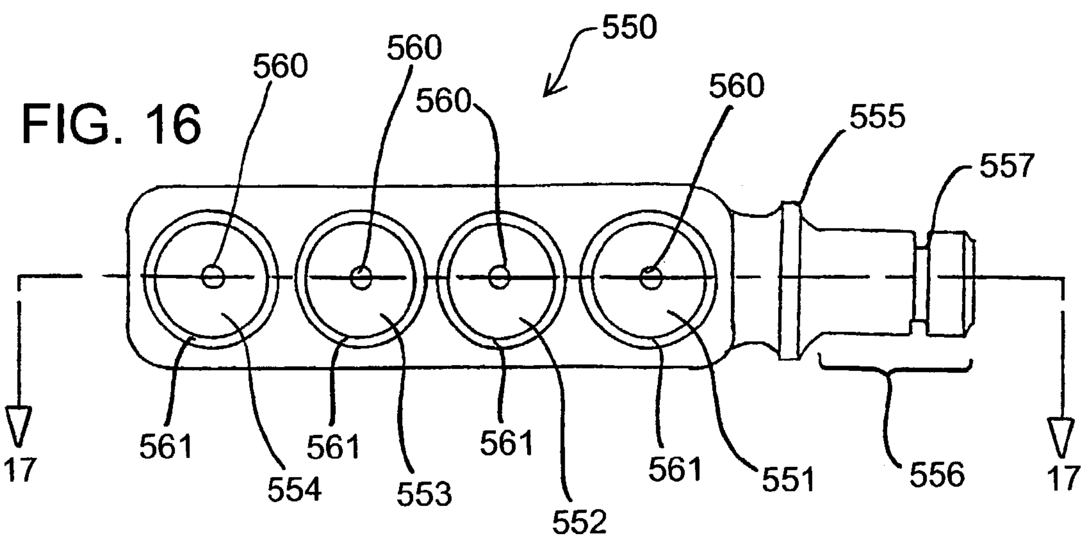
FIG. 16 is a bottom plan view of an alternate construction of a stabilizer foot according to the principles of the present invention.
Figure 17:
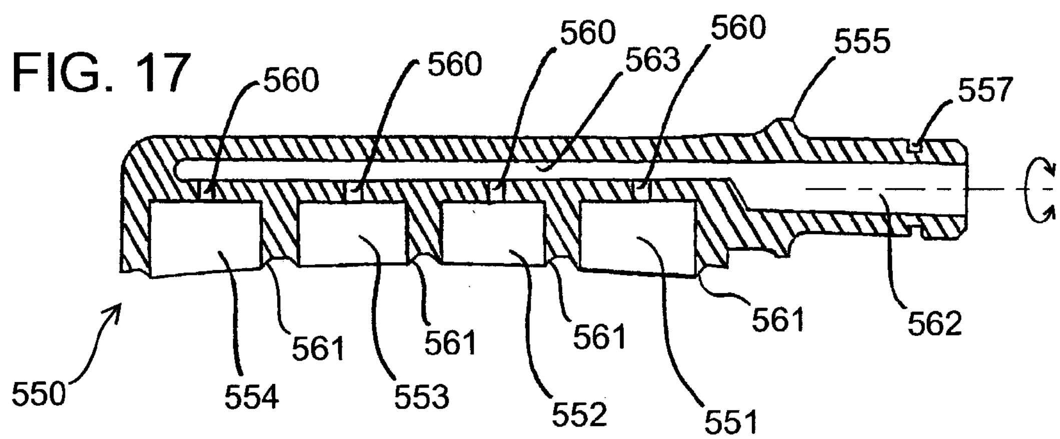
FIG. 17 is a cross-sectional view taken along line 17-17 as shown in FIG. 16.

FIGS. 16 and 17 illustrate stabilizer foot 550 having a plurality of individual vacuum ports. By way of example only, stabilizer foot 550 has four suction ports 551, 552, 553, and 554 each with a dedicated edge seal 561. Negative pressure is communicated to each port through openings or apertures 560 provided in vacuum distribution passage 563 which is fluid communication with vacuum inlet 562 which in turn is placed in fluid communication with the negative pressure within a manifold base assembly having a construction as described above. Stabilizer foot 550 may be mounted for rotation within a cooperating bore of an appropriate manifold base by way of cylindrical fitting portion 556 which may include a seal flange 555 and groove 557 for receiving an external retaining ring to secure fitting portion 556 in place.

Figure 18:
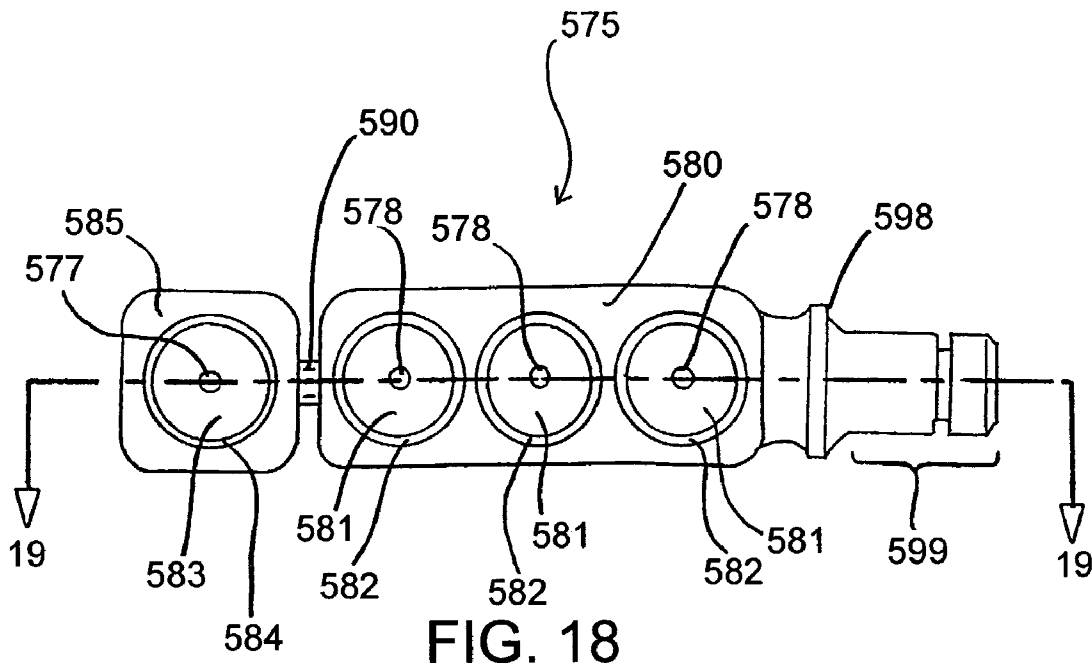
FIG. 18 is a bottom plan view of an alternate construction of a stabilizer foot.
Figure 19:
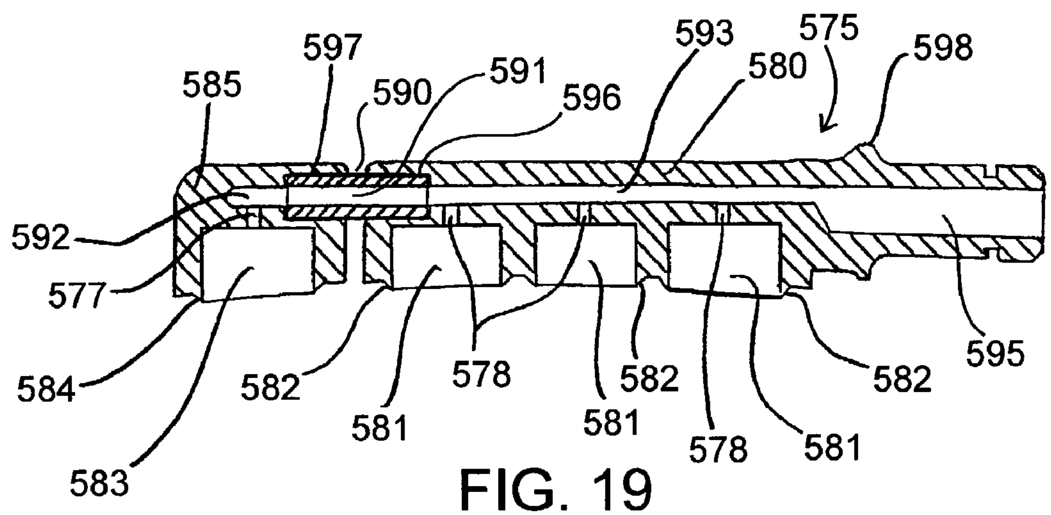
FIG. 19 is a cross-sectional view taken along line 19-19 as shown in FIG. 18.

FIGS. 18 and 19 show a variation of a stabilizer foot having a plurality of individual ports. Stabilizer foot 575 again has a fitting portion 599 having a seal flange 598 for retaining and compressing an appropriate shaft seal to provide the desired dynamic seal as stabilizer foot 575 is rotated about fitting portion 599. To facilitate even greater adjustment of the shape and orientation of stabilizer foot 575 has a first foot portion 580 with at least one vacuum port and a second foot portion 585 with at least one vacuum port which are adjustable relative to one another, preferably by way of one or more malleable joints or links.

In a preferred embodiment, first foot portion 580 has a plurality of separate vacuum ports 581 each with a perimeter seal 582. Preferably, first foot portion 580 has three vacuum ports 581 each supplied with negative pressure through apertures 578 in vacuum distribution channel or passage 593. Second foot portion 585 has at least one vacuum port 583 having perimeter seal 584 and aperture 577 in fluid communication with vacuum passage 592. First foot portion 580 and second foot portion 585 are preferably connected to each other by malleable tube 590, which has a lumen or passage 591 therethrough. Malleable tube 590 is preferably made of stainless steel, more preferably annealed stainless steel or vacuum annealed stainless steel.

With this configuration, the vacuum communicated from a manifold base or other vacuum source through vacuum inlet channel 595 is distributed to vacuum ports 581 and 583 through vacuum distribution channel 593 and associated apertures 578, through malleable tube passage 591, finally to vacuum passage 592 and associated aperture 577. The orientation of second foot portion 585 and thus vacuum port 583 can be adjusted relative to first foot portion 580 by simple bending it to the desired orientation. This additional adjustment tends to eliminate problems associated with obtaining a reliable seal at the tip of the stabilizer foot as the beating heart contracts away from the stabilizer, yet maintains the reliability of having ports 603 molded to a unitary relatively rigid stabilizing structure.

Malleable tube 590 may be secure to first foot portion 580 and second foot portion 585 in any convenient manner which provides a permanent and sealed connection. Preferably, the exterior of malleable tube 590 may be pressed into mating counterbores 596 and 597 provided in the ends of Vacuum passages 593 and 592 as shown. A suitable adhesive or bonding agent may additionally be used to sealingly secure malleable tube 590 in place. Alternatively, malleable tube 590 and counterbores 596 and 597 may be threaded together or malleable tube 590 could be insert molded within first and second foot portions 580 and 585.

Figure 20:
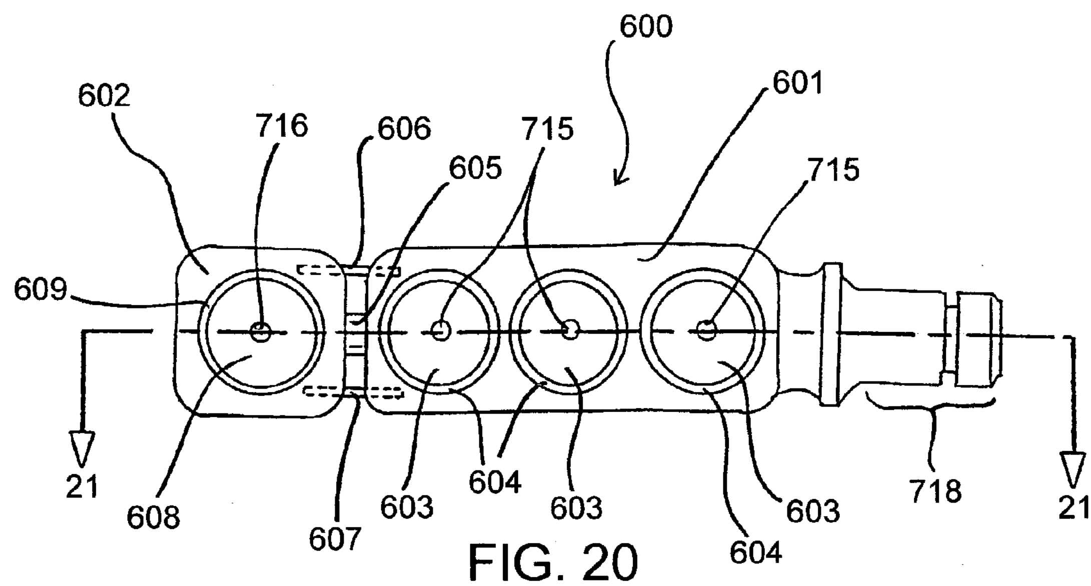
FIG. 20 is a bottom plan view of an alternate construction of a stabilizer foot.
Figure 21:
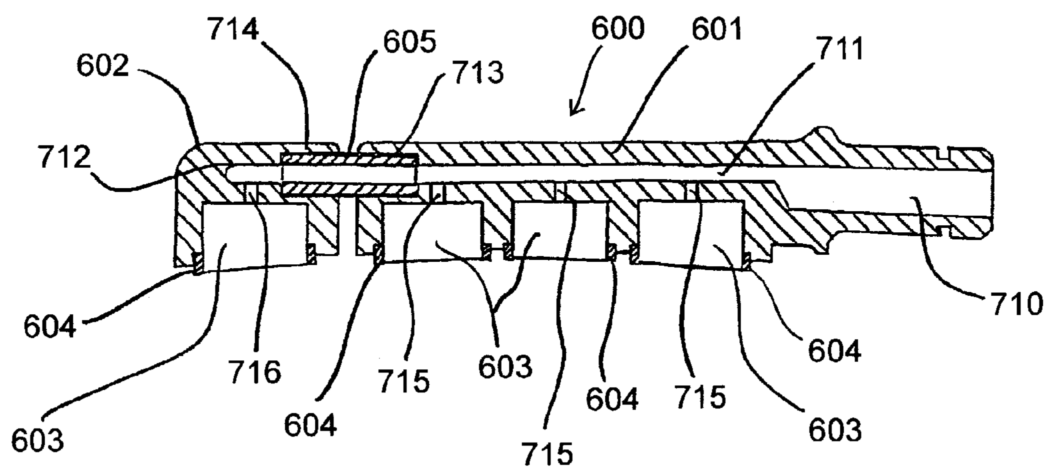
FIG. 21 is a cross-sectional view taken along line 21-21 as shown in FIG. 20.

FIGS. 20 and 21 illustrate another embodiment of a stabilizer foot having foot portions which are adjustable relative to one another to improve the fit, and accordingly the operating vacuum seal, against the surface of the tissue structure to be stabilized. Stabilizer foot 600 has a first foot portion 601 and a second foot portion 602. First foot portion 601 has one or more, preferably three, vacuum ports 603 and second foot portion 602 has one or more vacuum ports 608. Each of vacuum ports 603 and 608 preferably have a flexible or compressible perimeter seal 604 and 609, respectively, preferably made of a medical grade elastomer or foam. Negative pressure is supplied to vacuum ports 603 and 608 through openings or apertures 715 and 716 which in fluid communication with vacuum passages 711 and 712. Negative pressure is supplied to vacuum passage 711 through inlet channel or passage 710 of fitting portion 718. Fitting portion 718 connected to a vacuum chamber or source within a manifold base or like structure as described above.

First foot portion 601 and second foot portion 602 are made adjustable relative to each other by providing one or more malleable links spanning between the two portions. In one variation, first and second malleable members 606 and 607 are located off-center with respect vacuum ports 603 and 608. The off-center position of malleable members 606 and 607 better protects against excessive torsional loads applied to tube 605 if second foot portion 602 were twisted relative to first foot portion 601.

Malleable members 606 and 607 may be glued or bonded within cavities or bores provided within first and second foot portions 601 and 602 or may be insert molded during fabrication of the foot portions. Tube 605 fluidly connects vacuum passages 711 and 712. In this case, tube 605 may be malleable or may be a flexible tubing material. Preferably, tube 605 is assembled within counterbores 713 and 714.

In operation, the tissue stabilizers of the present invention allow the stabilizer feet, and in particular the features which operate to engage the surface of the tissue to be stabilized, to be optimally adjusted to for a specific surgical procedure or to adjust for variations in size and orientation of a patient's anatomy. In addition, the stabilizer feet can be adjusted after engagement to the tissue to be stabilized to produce an improved presentation of the tissue subject to the surgical procedure.

In a preferred method of operation for a tissue stabilizer having first and second rotatable stabilizer feet connected to a manifold base having a stabilizer shaft attached thereto, one or both of the stabilizer feet are adjusted to the desired orientation relative to the manifold base and each other. Preferably, the orientation of the stabilizer feet are adjusted to account for the size and shape of the tissue to be stabilized, for example a target site on the surface of the heart. If either of the stabilizer feet have an adjustable portion, it may also be adjusted at this time. Next, the tissue stabilizer is brought into engagement with the tissue to be stabilized and the vacuum is applied. The stabilizer shaft is then locked into place to immobilize the tissue stabilizer and the engaged tissue. With the surgical site now relatively motionless, one or both of the stabilizer feet may be rotated relative to the manifold base until the tissue between or adjacent the stabilizer feet obtains the best possible presentation for the procedure to be performed. If there appears to be any discernible vacuum leaks associated with the engagement of the stabilizer feet against the target tissue, the orientation of the stabilizer feet may be further adjusted or, if applicable, the feet portions may be adjusted, to eliminate or minimize vacuum leaks at the interface between the stabilizer feet and the target tissue.

Figure 22:
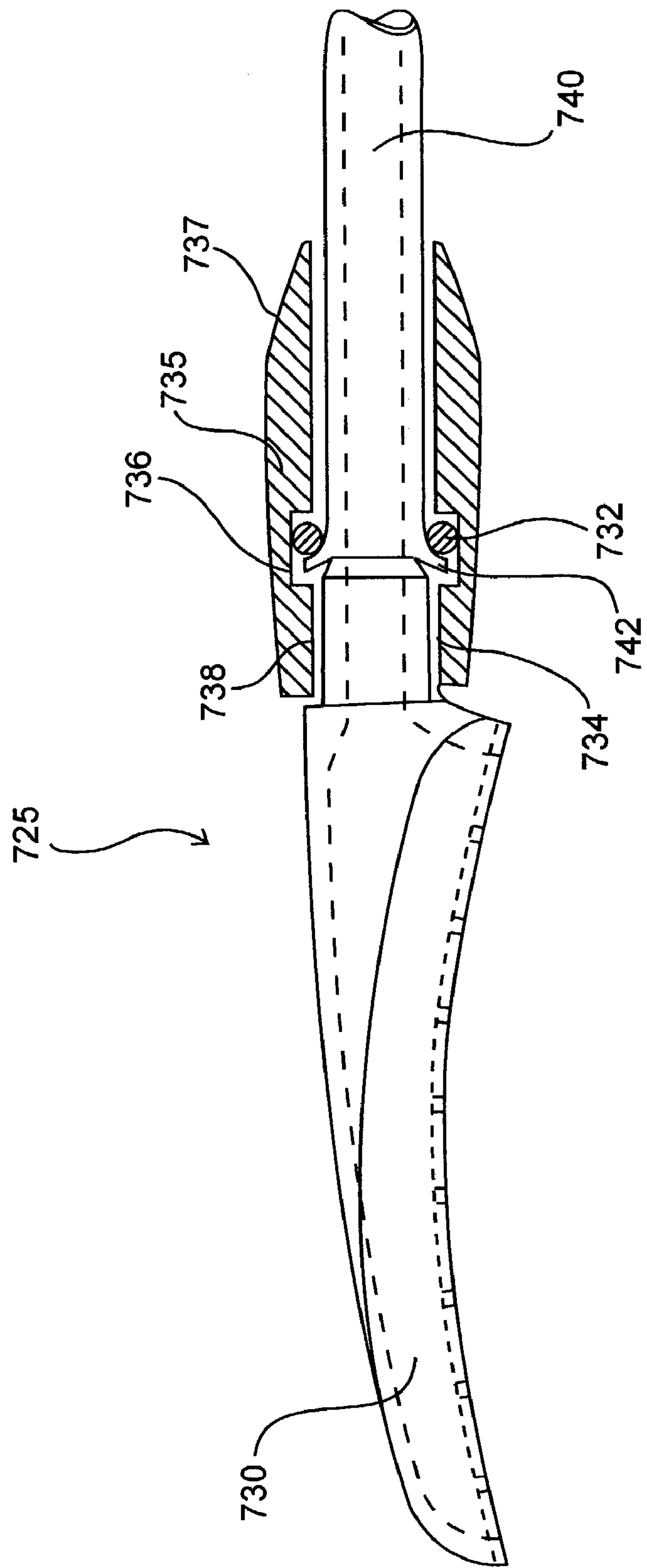
FIG. 22 is a partial cross-sectional view of an alternate construction of a tissue stabilizer according to the principles of the present invention.

Although the illustrative stabilizer feet described above have been primarily directed to embodiments configured for connection to a common manifold base, the stabilizer feet of the present invention will operate with equal benefit when connected to any number of alternative structures. For example, FIG. 22 illustrates tissue stabilizer 725 having a stabilizer foot rotatably connected with respect to a portion of common tubing having a flared end. Tube 740 may be a malleable tube, for example made of annealed stainless steel, which may be connected proximally to a manifold (not shown) shared with a second stabilizer foot or may be connected directly to a fixed mount (not shown) to effectuate stabilization.

In a preferred embodiment, stabilizer foot 730 is connected to housing 735 which rotates about tube 740. Tube 740 has a flared end 742 as is commonly known in the art. A shaft seal, such as O-ring 732, is place over tube 740 adjacent flared end 742. Housing 735 has a first bore 737 and a second larger bore 738. First bore 737 is larger than the outside diameter of tube 740 but preferably smaller than the diameter of flanged end 742. Second bore 738 is preferably slightly larger than flanged end 742. Tube 740 with O-ring 732 is assembled through second bore 738 until the O-ring is compressed at the distal entrance to first bore 737. An O-ring cavity 736 may be provided if desired. Fitting portion 734 is inserted into second bore 738 and permanently fixed in place preferably using a fluid tight connection such as pipe threads, adhesive, bonding agent, welding, brazing, etc. With fitting portion 734 fixed to housing 735, stabilizer foot 730 and housing 735 may be rotated relative to tube 740 without any appreciable vacuum leakage. Stabilizer foot 730 may be of any desirable configuration.

While certain embodiments are illustrated in the drawings and have just been described herein, it will be apparent to those skilled in the art that many modifications can be made to the embodiments without departing from the inventive concepts described. For purposes of illustration only, the principles of the present invention has been described with reference to stabilizing the heart during a coronary artery bypass procedure but may readily be applied to other types surgical procedures on various types of tissue structures not specifically described. Many other uses are well-known in the art, and the concepts described herein are equally applicable to those other uses. Further, the different components and their equivalents of the various exemplar embodiments described above can be combined to achieve any desirable construction.

What is claimed is:

1. A device for stabilizing tissue within a patient's body, said device comprising:

a base member; and an elongated stabilizer foot comprising a first rigid foot portion and a second rigid foot portion, wherein at least one of said first and second foot portions comprises a plurality of separate openings for delivery of negative pressure to a surface of a tissue, each of said plurality of separate openings having a dedicated edge seal, said first and said second foot portions being adjustable relative to one another by way of one or more malleable joints, said elongated stabilizer foot extending outwardly from said base member in a first direction and fluidically connected with said base member, said foot being rotatable, in its entirety, relative to said base member, about an axis of rotation which is oriented in substantially the same direction as said first direction.

2. The device of claim 1, wherein said first and said second rigid foot portions each comprise at least one vacuum port.

3. The device of claim 1, wherein said vacuum ports independently engage said tissue.

4. The device of claim 1, wherein said malleable joint comprises a malleable tube.

5. The device of claim 1, wherein said malleable joint is made of stainless steel.

6. The device of claim 5, wherein said malleable joint is made of annealed stainless steel or vacuum annealed steel.

7. A device for stabilizing tissue within a patient's body, said device comprising:

a base member; and an elongated stabilizer foot comprising a first substantially inflexible foot portion having a first length and a second substantially inflexible foot portion having a second length, wherein said second length is shorter than said first length and wherein said first and second foot portions are interconnected by at least one flexible joint permitting positioning of said second foot portion relative to said first foot portion about at least two degrees of freedom; one of said first and second foot portions being connected to said base member.

8. The device of claim 7, wherein said first foot portion connects with said base member and said second foot portion extends distally from said first foot portion.

9. The device of claim 7, comprising a pair of said elongated stabilizer feet extending from said base member.

10. The device of claim 7, wherein said foot comprises at least one opening for delivery of negative pressure to a surface of the tissue, said at least one opening being fluidly connectable with a source of negative pressure.

11. A device for stabilizing tissue within a patient's body, said device comprising:

a base member; and an elongated stabilizer foot comprising at least two elongated substantially inflexible foot portions interconnected by at least one flexible section allowing one of said at least two elongated substantially inflexible foot portions to be adjusted relative to another of said at least two elongated substantially inflexible foot portions to adjust for variations in size and orientation of the patient's anatomy, wherein said elongated stabilizer foot comprises at least two separate openings for delivery of negative pressure to a surface of a tissue that are not rotatable with respect to one another, said at least two separate openings being connected to a negative pressure distribution passage via independent passages fluidly connecting said negative pressure distribution passage with said at least two separate openings.

12. The device of claim 11, wherein said each said elongated substantially inflexible foot portion comprises at least one opening for delivery of negative pressure to a surface of the tissue, each said opening being fluidly connectable with a source of negative pressure.

13. The device of claim 12, wherein said at least one flexible section is fluidly connected with said inflexible foot portions.

14. The device of claim 11, wherein said elongated stabilizer foot is rotatable with respect to said base member.

15. A device for stabilizing tissue within a patient's body, said device comprising:

a base member; and an elongated stabilizer foot comprising a first foot portion and a second foot portion interconnected by and fixed to a flexible section comprising a member that is flexible, wherein said first and second foot portions are relatively rigid, such that a portion of said first foot portion cannot rotate relative to a remainder of said first foot portion and a portion of said second foot portion cannot rotate relative to a remainder of said second foot portion, wherein said elongated stabilizer foot is rotatably connected to said base member; and wherein said first foot portion has a first length and said second foot portion has a second length, said first length being greater than said second length.

16. The device of claim 15, wherein said flexible section comprises a malleable vacuum tube.

17. The device of claim 16, wherein said first and second foot portions each comprise an opening for delivery of negative pressure to a surface of the tissue, said malleable vacuum tube fluidly interconnecting said openings in said first and second foot portions.

18. A device for stabilizing tissue within a patient's body, said device comprising:

an elongated, malleable stabilizer foot comprising a first foot portion and a second foot portion interconnected by and fixed to a flexible section, said flexible section comprising a malleable tube permanently and sealably connecting said first and second foot portions, and wherein said elongated stabilizer includes a fitting for insertion into an opening in a base member, thereby rotatably connecting to said base member.

19. The device of claim 18, wherein said malleable section comprises a malleable vacuum tube.

20. The device of claim 18, wherein said first and second foot portions each comprise an opening for delivery of negative pressure to a surface of the tissue.

21. The device of claim 20, wherein said openings are fluidly interconnected with an opening in a proximal end portion of said elongated, malleable stabilizer foot for fluid connection with said base member.

22. The device of claim 20, wherein said flexible section comprises a malleable vacuum tube fluidly interconnecting said openings in said first and second foot portions.

23. A device for stabilizing tissue within a patient's body, said device comprising:

a base member; and an elongated stabilizer foot comprising at least two elongated substantially inflexible foot portions interconnected by at least one flexible section, wherein said elongated stabilizer foot comprises at least two separate openings for delivery of negative pressure to a surface of a tissue that are not rotatable with respect to one another, said at least two separate openings being connected to a negative pressure distribution passage via independent passages fluidly connecting said negative pressure distribution passage with said at least two separate openings, and wherein each said elongated substantially inflexible foot portion comprises at least one opening for delivery of negative pressure to a surface of the tissue, each said opening being fluidly connectable with a source of negative pressure.

* * * * *